United States Patent
Kurz et al.

(10) Patent No.: US 6,429,300 B1
(45) Date of Patent: Aug. 6, 2002

(54) PEPTIDE ACCEPTOR LIGATION METHODS

(75) Inventors: Markus Kurz, West Newton; Peter Lohse, Weston; Richard Wagner, Concord, all of MA (US)

(73) Assignee: Phylos, Inc., Lexington, MA (US)

( * ) Notice: Subject to any disclaimer, the term of this patent is extended or adjusted under 35 U.S.C. 154(b) by 0 days.

(21) Appl. No.: 09/619,103

(22) Filed: Jul. 19, 2000

Related U.S. Application Data

(60) Provisional application No. 60/145,834, filed on Jul. 27, 1999.

(51) Int. Cl.[7] .............................................. C07H 21/02
(52) U.S. Cl. ..................... 536/23.1; 435/68.1; 435/91.9
(58) Field of Search .................... 536/23.1; 435/91.9, 435/68.1

(56) References Cited

U.S. PATENT DOCUMENTS

| | | | |
|---|---|---|---|
| 5,843,701 A | 12/1998 | Gold et al. | 435/68.1 |
| 5,985,575 A | 11/1999 | Wickens et al. | 435/6 |
| 6,207,446 B1 * | 3/2001 | Szostak et al. | 435/287.2 |

FOREIGN PATENT DOCUMENTS

| | | |
|---|---|---|
| WO | WO 98/31700 | 7/1998 |

OTHER PUBLICATIONS

Rachel Green et al. Ribosome–Catalyzed Peptide–Bond Formation with an A–Site Substrate Covalently Linked to 23S Ribosomal RNA Science vol. 280 Apr. 10, 1998 pp. 286–289.*

Bauman et al., "Cytochemical hybridization with fluorochrome–labeled RNA," *The Journal of Histochemistry and Cytochemistry* 29(2):227–237 (1981).

Cox et al., "Characterization of IL–2 receptor expression and function on murine macrophages," *The Journal of Immunology* 145(6):1719–1726 (1990).

Gamper et al., "Efficient formulation of a crosslinkable HMT monoadduct at the Kpn I recognition site," *Photochemistry and Photobiology* 40(1):29–34 (1984).

Godard et al., "Photochemically and chemically activatable antisense oligonucleotides: comparison of their reactivities towards DNA and RNA targets," *Nucleic Acids Research* 22(22):4789–4795 (1994).

Ghosh et al., "Synthesis of 5–oligonucleotide hydrazide derivatives and their use in preparation of enzyme–nucleic acid hybridization probes," *Analytical Biochemistry* 178:43–51 (1989).

Hanvey et al., "Antisense and antigene properties of peptide nucleic acids," *Science* 258:1481–1485 (1992).

Knudsen et al., "Antisense properties of duplex–and triplex–forming PNAs," *Nucleic Acids Research* 24(3):494–500 (1996).

Pascolo et al., "Relative contribution of photo–addition, helper oligonucleotide and RNase H to the antisense effect of psoralen–oligonucleotide conjugates, on in vitro translation of Leishmania mRNAs," *Biochimica et Biophysica Acta* 1219:98–106 (1994).

Pieles et al., "Psoralen covalently linked to oligodeoxyribonucleotides: synthesis, sequence specific recognition of DNA and photo–cross–linking to pyrimidine residues of DNA," *Nucleic Acids Research* 17(1):285–299 (1989).

Proudnikov et al., "Chemical methods of DNA and RNA fluorescent labeling," *Nucleic Acids Research* 24(22):4535–4542 (1996).

Roberts et al., "RNA–peptide fusions for the in vitro selection of peptides and proteins," *Proc. Natl. Acad. Sci. USA* 94:12297–12302 (1997).

Sinden et al., "Interstrand psoralen cross–links do not introduce appreciable bends in DNA," *Biochemistry* 23:6299–6303 (1984).

Uhlmann et al., "Synthesis and properties of PNA/DNA chimeras," *Agnew. Chem. Int. Ed. Engl.* 35(22):2632–2635 (1996).

Wu et al., "A fluorence–labeling method for sequencing small RNA on polyacrylamide gel," *Nucleic Acids Research* 24(17):3472–3473 (1996).

* cited by examiner

*Primary Examiner*—Remy Yucel
*Assistant Examiner*—Bronwen M. Loeb
(74) *Attorney, Agent, or Firm*—Clark & Elbing LLP

(57) ABSTRACT

Described herein are methods and reagents for the ligation of a peptide acceptor to an RNA, as well as the RNA-peptide acceptor products.

43 Claims, 14 Drawing Sheets

⊕ = REACTIVE FUNCTIONAL GROUP (SEE FIGURES 3A & 3B)

PEPTIDE ACCEPTOR LIGATION METHODS

CROSS REFERENCE TO RELATED APPLICATIONS

This application claims the benefit of the filing date of provisional application, U.S. Ser. No. 60/145,834, filed Jul. 27, 1999.

BACKGROUND OF THE INVENTION

In general, the present invention relates to ligation methods, in particular, for joining peptide acceptors to nucleic acids. Methods currently exist for the preparation of RNA-protein fusions. An RNA-protein fusion is created by attaching a peptide acceptor to the 3' end of an RNA molecule, followed by in vitro or in situ translation of the RNA. The product is a peptide attached to the 3' end of the RNA encoding it. The generation of these RNA-protein fusions facilitates the isolation of proteins with desired properties from large pools of partially or completely random amino acid sequences, and solves the problem of recovering and amplifying protein sequence information by covalently attaching the RNA coding sequence to its corresponding protein molecule.

SUMMARY OF THE INVENTION

The present invention features methods for the attachment of a peptide acceptor to an RNA molecule as well as the RNA-peptide acceptor products. These methods facilitate the production of RNA-protein fusions which can be used, for example, for the isolation of proteins or nucleic acids with desired properties from large pools of partially or completely random amino acid or nucleic acid sequences. This inventive method may be carried out by a variety of strategies for affixing a peptide acceptor to a nucleic acid molecule. These various approaches differ from one another in the types of bonds formed by the attachment of the peptide to the nucleic acid, and in the reagents used to achieve the attachment.

Accordingly, in a first aspect, the invention features a method for affixing a peptide acceptor to an RNA molecule involving providing an RNA molecule having a 3' sequence which forms a hairpin structure, providing a peptide acceptor covalently bonded to a nucleic acid linker molecule, and hybridizing the RNA molecule to the nucleic acid linker molecule under conditions which allow covalent bond formation to occur between the peptide acceptor and the RNA molecule.

In a second aspect, the invention features a method for affixing a peptide acceptor to an RNA molecule involving providing a peptide acceptor having a linker with a 5' sequence that forms a hairpin, hybridizing the peptide acceptor to the RNA molecule, and covalently bonding the peptide acceptor to the RNA. In one embodiment of the above aspects of the invention, the peptide acceptor is bonded to the RNA molecule using T4 DNA ligase.

In a third aspect, the invention features a method for attaching a peptide acceptor to an RNA molecule, by providing an RNA molecule and a peptide acceptor covalently bonded to a linker molecule, where the linker molecule initiates with a deoxynucleotide triphosphate or dideoxynucleotide triphosphate, and contacting the RNA molecule and peptide acceptor with terminal deoxynucleotidyl transferase to covalently bond the peptide acceptor to the RNA molecule.

In a fourth aspect, the invention features a method of affixing a peptide acceptor to an RNA molecule by chemically ligating the RNA molecule to the peptide acceptor.

In one embodiment of this aspect, the peptide acceptor is joined to a psoralen moiety and crosslinked to the RNA molecule via the psoralen moiety. The psoralen moiety may be attached to either the 5' or 3' end of a linker molecule which is itself attached to the peptide acceptor, or the psoralen moiety may be located at an internal position of the linker molecule. According to this technique, the peptide acceptor is crosslinked to the RNA molecule using UV irradiation. In further embodiments of this particular aspect, the psoralen is attached to the peptide acceptor through a C6 alkyl chain and/or the RNA molecule contains a stop codon positioned proximal to its 3' end. Preferably, the linker is between 25 and 40 nucleotide units in length. In addition, prior to crosslinking the peptide acceptor to the RNA molecule, the RNA may be hybridized to a linker that further includes a photocleavable moiety. The hybridized RNA may then be immobilized to a solid support through the photocleavable moiety. Preferably, the photocleavable moiety is biotin.

In another embodiment of the fourth aspect of the invention, the RNA molecule is functionalized and is attached to a peptide that has been suitably modified to permit chemical bond formation between the peptide acceptor and the RNA molecule. Preferably, the RNA molecule is functionalized through $IO_4^-$ oxidation. The peptide acceptor may be functionalized by attaching a molecule to the peptide acceptor chosen from the group consisting of amines, hydrazines, (thio)hydrazides, and (thio)semicarbazones.

In yet another embodiment of the fourth aspect of the invention, the chemical ligation is carried out in the absence of an external template. Alternatively, the chemical ligation reaction can be carried out in the presence of an external template. This second method involves aligning the RNA molecule and the linker portion of a peptide acceptor using a template, so that the 5' end of the template hybridizes to the linker portion of the peptide acceptor and the 3' end of the template hybridizes to the RNA molecule. The chemical ligation of an RNA molecule to a peptide acceptor can also be carried out in the absence of an external template by hybridizing the linker molecule itself, which is covalently bonded to the peptide acceptor, to the RNA molecule. This hybridization brings the peptide acceptor and RNA molecule into close proximity for ligation. Preferably, the functional group is at the 5' end of the linker region of the peptide acceptor, or is flanked by a hybridization domain on one side and the peptide acceptor on the other side.

In a further embodiment of the fourth aspect of the invention, the chemical ligation of the peptide acceptor to the RNA molecule involves attaching a functional group to the RNA molecule through reductive amination of the RNA, followed by modification of the peptide acceptor to react with the RNA molecule. The two molecules are then joined through formation of a covalent bond. Preferably, the functional group attached to the RNA molecule is a thiol, maleimide, or amine.

In a fifth aspect, the invention features a method for attaching a peptide acceptor to an RNA molecule through a non-covalent bond. In one embodiment, the attachment is achieved by covalently bonding a peptide nucleic acid (PNA) to the peptide acceptor and non-covalently bonding the peptide acceptor to the RNA molecule through the PNA. In this embodiment, the RNA molecule may contain a stop codon.

In yet other aspects, the invention features RNA molecules chemically or non-covalently ligated to peptide acceptors as well as the nucleic acid-protein fusions generated by transcription and translation (and, if desired, reverse transcription and/or amplification) of these RNA molecules. In one embodiment, the peptide acceptor is ligated at the 3' end of the RNA molecule.

In still another aspect, the invention features methods for the selection of a desired protein or nucleic acid using the RNA-peptide acceptor molecules of the invention. The selection techniques utilize the present molecules for RNA-protein fusion formation, and subsequent selection of proteins or nucleic acids of interest. The selection methods may be carried out by any of the approaches described, for example, in Szostak et al., WO 98/31700, and Szostak et al., U.S. Ser. No. 09/247,190 now U.S. Pat. No. 6,261,804, hereby incorporated by reference.

In a final aspect, the invention features a method of generating an RNA-protein fusion. This method involves providing an RNA molecule hybridized to a linker, where the linker contains a photocleavable moiety, a psoralen moiety, and a peptide acceptor; immobilizing the RNA to a solid support under conditions in which non-immobilized RNA are substantially removed from the support; crosslinking the peptide acceptor to the RNA, through the psoralen moiety, whereby this crosslinking simultaneously releases the crosslinked RNA from the solid support; and translating the crosslinked RNA to form an RNA-fusion protein. In one embodiment, the photocleavable moiety is biotin.

In all of the above aspects of the invention, the RNA molecule may include a translation initiation sequence and a start codon operably linked to a candidate protein coding sequence. In addition, one preferred peptide acceptor is puromycin, a nucleoside analog which adds to the C-terminus of a growing peptide chain and terminates translation. In one embodiment, the peptide acceptor includes puromycin attached to a linker, for example, a nucleotide linker. This linker facilitates the alignment of the peptide acceptor to the RNA molecule for attachment. In a further embodiment, the linker region of the peptide acceptor includes non-nucleotide moieties, for example, PEG. Other possible choices for acceptors include tRNA-like structures at the 3' end of the RNA, as well as other compounds that act in a manner similar to puromycin. Such compounds include, without limitation, any compound which possesses an amino acid linked to an adenine or an adenine-like compound, such as the amino acid nucleotides, phenylalanyl-adenosine (A-Phe), tyrosyl adenosine (A-Tyr), and alanyl adenosine (A-Ala), as well as amide-linked structures, such as phenylalanyl 3' deoxy 3' amino adenosine, alanyl 3' deoxy 3' amino adenosine, and tyrosyl 3' deoxy 3' amino adenosine; in any of these compounds, any of the naturally-occurring L-amino acids or their analogs may be utilized. In addition, a combined tRNA-like 3' structure-puromycin conjugate may also be used in the invention.

In one preferred design of the invention, a DNA sequence is included between the end of the message and the peptide acceptor. This sequence is designed to cause the ribosome to pause at the end of the open reading frame, providing additional time for the peptide acceptor (for example, puromycin) to accept the nascent peptide chain before hydrolysis of the peptidyl-tRNA linkage. During in vitro translation the ribosome may also pause at the site of chemical ligation, especially at a psoralen crosslinking site or at a PNA clamp.

In another preferred design of the invention, predominantly non-nucleotide linker moieties may be used in place of the nucleotide linkers attached to the peptide acceptor. This design facilitates the ligation of a peptide acceptor to an RNA molecule. For example, the linker may contain triethylene glycol spacers. The linker may also contain 2'-OMe-RNA phosphoramidites. In some cases where hybridization is a prerequisite for chemical or enzymatic ligation, a sufficient portion of the linker next to the ligation site must be comprised of nucleic acids. Furthermore, the RNA or linker of the invention may contain a sequence (e.g., a poly(A) sequence) for use in purification, for example, affinity purification of the RNA or an RNA-protein fusion molecule formed from such an RNA or linker.

In addition, in all of the above aspects of the invention the RNA molecule affixed to a peptide acceptor may be in vitro or in situ translated to produce an RNA-protein fusion molecule. The RNA-protein fusion molecule is then incubated in the presence of high salt and/or incubated at low temperature (e.g., overnight at −20° C.) as described by Szostak et al. (09/247,190, now U.S. Pat. No. 6,261,804). The RNA-protein fusion molecule may be also purified, for example, using standard poly(A) purification techniques.

As used herein, by a "protein" is meant any two or more naturally occurring or modified amino acids joined by one or more peptide bonds. "Protein" and "peptide" are used interchangeably.

By an "RNA" is meant a sequence of two or more covalently bonded, naturally occurring or modified ribonucleotides. One example of a modified RNA included within this term is phosphorothioate RNA.

By a "translation initiation sequence" is meant any sequence that is capable of providing a functional ribosome entry site. In bacterial systems, this region is sometimes referred to as a Shine-Dalgamo sequence.

By a "start codon" is meant three bases which signal the beginning of a protein coding sequence. By a "stop codon" is meant three bases which signal the termination of a protein coding sequence. Generally, start codons are AUG (or ATG) and stop codons are UAA (or TAA), UAG (or TAG), or UGA (or TGA); however, any other base triplets capable of being utilized as start or stop codons may be substituted.

By "covalently bonded" is meant joined together either directly through a covalent bond or indirectly through another covalently bonded sequence (for example, DNA corresponding to a pause site).

A By "non-covalently bonded" is meant joined together by means other than a covalent bond.

By a "hairpin structure" is meant a double-stranded region formed by a single nucleic acid strand. Preferably, such hairpin structures are at least 8 base pairs in length, and more preferably, between 8 and 15 base pairs in length.

By "chemically ligating" is meant the joining together of two molecules without the use of an enzyme. Chemical ligation can result in non-covalent as well as covalent bonds.

By a "peptide acceptor" is meant any molecule capable of being added to the C-terminus of a growing protein chain by the catalytic activity of the ribosomal peptidyl transferase function. Typically, such molecules contain (i) a nucleotide or nucleotide-like moiety, for example adenosine or an adenosine analog (di-methylation at the N-6 amino position is acceptable), (ii) an amino acid or amino acid-like moiety, such as any of the 20 D- or L-amino acids or any amino acid analog thereof including 0-methyl tyrosine or any of the analogs described by Ellman et al. (Meth. Enzymol. 202:301, 1991), and (iii) a linkage between the two (for example, an ester, amide, or ketone linkage at the 3' position or, less preferably, the 2' position). Preferably, this linkage does not significantly perturb the pucker of the ring from the natural ribonucleotide conformation. Peptide acceptors may also possess a nucleophile, which may be, without limitation, an amino group, a hydroxyl group, or a sulfhydryl group. In addition, peptide acceptors may be composed of nucleotide mimetics, amino acid mimetics, or mimetics of the combined nucleotide-amino acid structure.

By a "linker" or "linker molecule" is meant a sequence that includes deoxyribonucleotides, ribonucleotides, or analogs thereof By "functionalize" is meant to modify in a manner that results in the attachment of a functional group or moiety. For example, an RNA molecule may be functionalized through $IO_4^-$ oxidation or amination, or a peptide acceptor may be functionalized by attaching an amine, hydrazine, (thio)hydrazide, or (thio)semicarbazone group.

By an "external template," is meant a nucleic acid sequence which is added to a ligation reaction mixture, but which is not a part of the final product of the ligation reaction.

By "high salt" is meant having a concentration of a monovalent cation of at least 200 mM, and, preferably, at least 500 mM or even 1 M, and/or a concentration of a divalent or higher valence cation of at least 25 mM, preferably, at least 50 mM, and, most preferably, at least 100 mM.

By "affinity purification sequence" is meant a nucleotide sequence that is utilized in the purification of a nucleic acid or a nucleic acid-protein fusion molecule. For example, an affinity purification sequence may be a poly(A) sequence, such as $A_{8-20}$ (SEQ ID NOS: 16–26), which can be used for purification of nucleic acid or fusion molecules on oligo-dT cellulose. An affinity purification sequence may also be a polypeptide sequence that is used to purify a nucleic acid-protein fusion molecule. Other exemplary purification techniques are described by Szostak et al. U.S. Ser. No. 09/247, 190, now U.S. Pat. No. 6,261,804.

The present invention provides a number of advantages. For example, the methods described herein facilitate the efficient ligation of peptide acceptors to RNA molecules, in some aspects, without the need for an external template to bring the RNA and peptide acceptor together. The invention also reduces the cost associated with the generation of an RNA-protein fusion.

Other features and advantages of the invention will be apparent from the following detailed description, and from the claims.

DETAILED DESCRIPTION

The drawings will first briefly be described.

Described herein are various methods of attaching a peptide acceptor to an RNA molecule. The RNA may be generated by any standard approach, including normal cellular synthesis, recombinant techniques, and chemical synthesis, and includes, without limitation, cellular RNA, mRNA libraries, and random synthetic RNA libraries. The peptide acceptor (for example, puromycin) is typically bonded to a DNA or RNA linker. Such peptide acceptor molecules may be generated by any standard technique, for example, the techniques described in Roberts and Szostak (Proc. Natl. Acad. Sci. USA 94:12297, 1997), Szostak et al. (WO 98/31700), and Szostak et al., U.S. Ser. No. 09/247, 190, now U.S. Pat. No. 6,261,804. Techniques for carrying out each method of the invention are now described in detail, using particular examples. These examples are provided for the purpose of illustrating the invention, and should not be construed as limiting.

EXAMPLE 1

Enzymatic Ligation Methods Involving T4 DNA Ligase on a Hairpin Template

Figure 1:
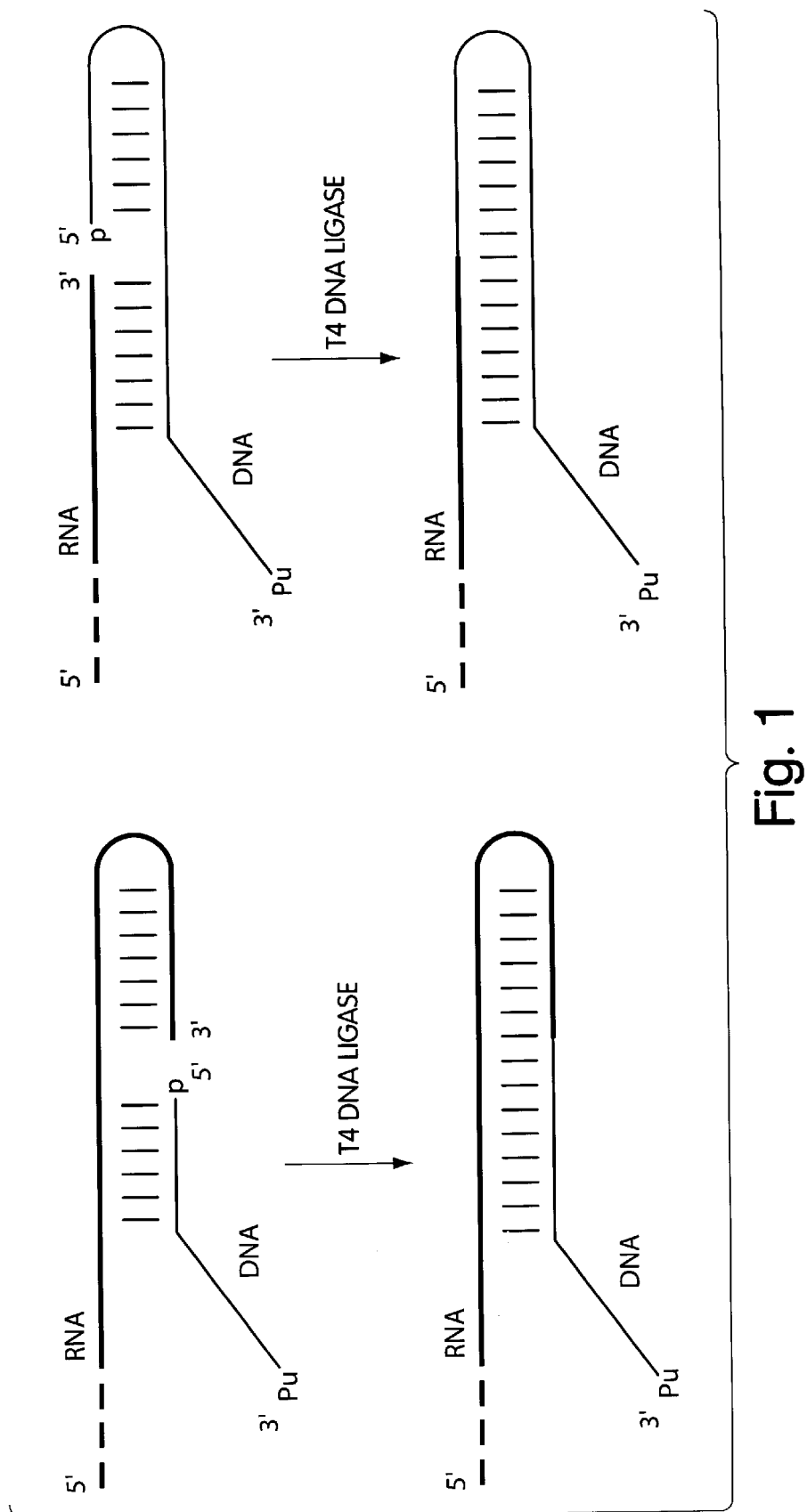
FIG. 1 is a schematic representation of exemplary steps involved in the ligation of a peptide acceptor linker to an RNA using T4 DNA ligase on a hairpin template. Either the RNA 3' sequence or the peptide acceptor linker is designed to form a hairpin structure, and the peptide acceptor linker hybridizes to the RNA, thus bringing the RNA and peptide acceptor into close proximity to each other.

In one particular approach according to the invention, T4 DNA ligase is used to attach a peptide acceptor to an RNA molecule using a hairpin-containing template, for example, as shown in FIG. 1. The ligation reaction is carried out in a self-templating manner and does not utilize a splint oligo. Either the RNA 3' sequence or the 5' end of the linker region of the peptide acceptor is designed to form a hairpin structure. Close positioning of the 5' end of the linker region of the peptide acceptor and the 3' end of the RNA in the context of a hairpin structure facilitates enzymatic ligation with T4 DNA ligase, as described, for example, in Sambrook, Fritsch, & Maniatis, *Molecular Cloning*, Cold Spring Harbor, New York, Cold Spring Harbor Laboratory Press, 1989. The ratio of the reactants is approximately 1:1, although a slight excess (1:1.2) of either reactant is acceptable. Optimal ligation conditions may vary slightly from reaction to reaction and may be determined experimentally using techniques known to those skilled in the art.

EXAMPLE 2

Enzymatic Ligation Methods Involving Terminal Transferase

Figure 2:
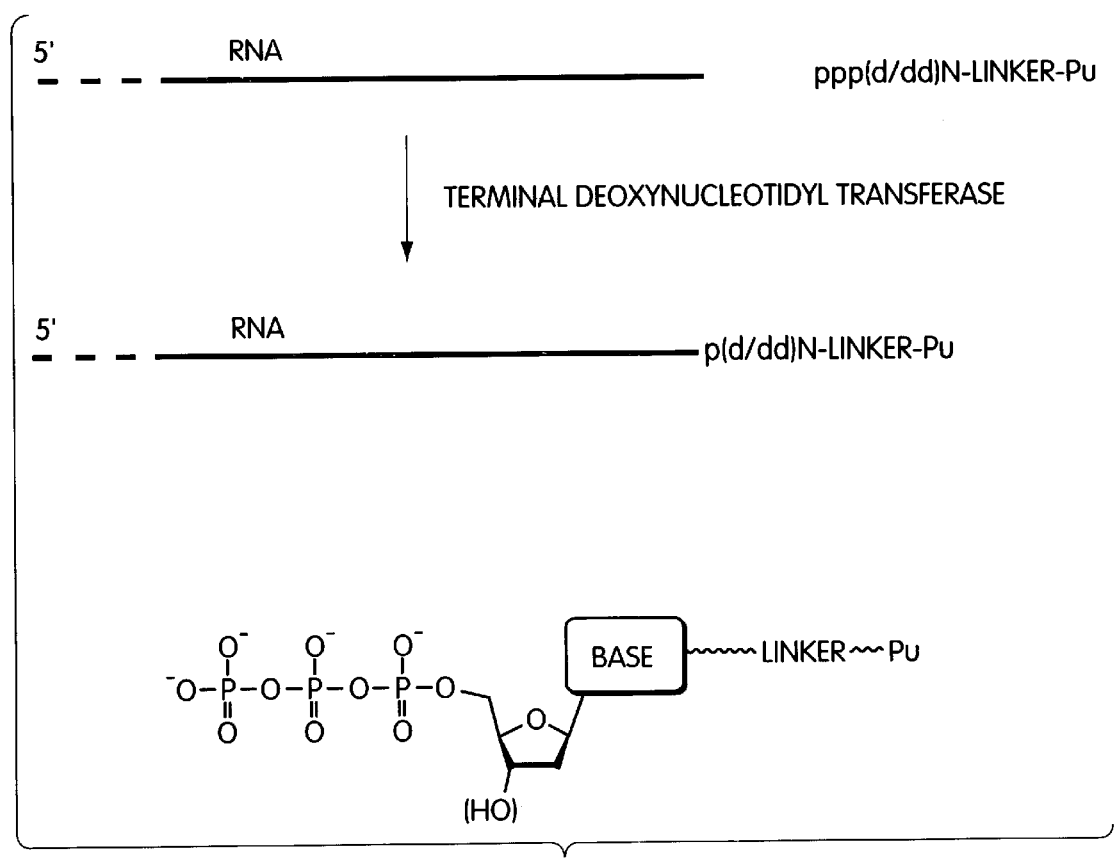
FIG. 2 is a schematic representation of exemplary steps involved in the ligation of a peptide acceptor linker to an RNA using terminal deoxynucleotidyl transferase.

Another enzymatic method for the attachment of a peptide acceptor to an RNA molecule involves the modification of the 3' end of the RNA followed by ligation using terminal deoxynucleotidyl transferase, for example, as shown in FIG. 2. The TdT reaction is carried out as generally described in Sambrook, Fritsch, & Maniatis (sura). This enzyme extends the 3' end of nucleic acids with deoxy- (or dideoxy-) nucleotide triphosphates. These (d/dd)NTPs may be chemically modified on their base moieties to carry the desired linker structures (as described, for example, in Meyer, *Methods in Molecular Biology*, Agrawal, ed., vol 26, Totowa: Humana Press, 1994, pages 73–91; Kumar et al., Anal. Biochem. 169:376, 1988; Riley et al., DNA 5:333, 1986; and Schmitz et al., Anal. Biochem. 192:222, 1991). As shown in FIG. 2, the linker molecule must initiate with a (d/dd) NTP. The remainder of the linker composition, however, may vary. A special feature of this terminal transferase ligation method is that the DNA linker region of the peptide acceptor can be as short as one (d/dd)NTP unit.

EXAMPLE 3

Figure 3A:
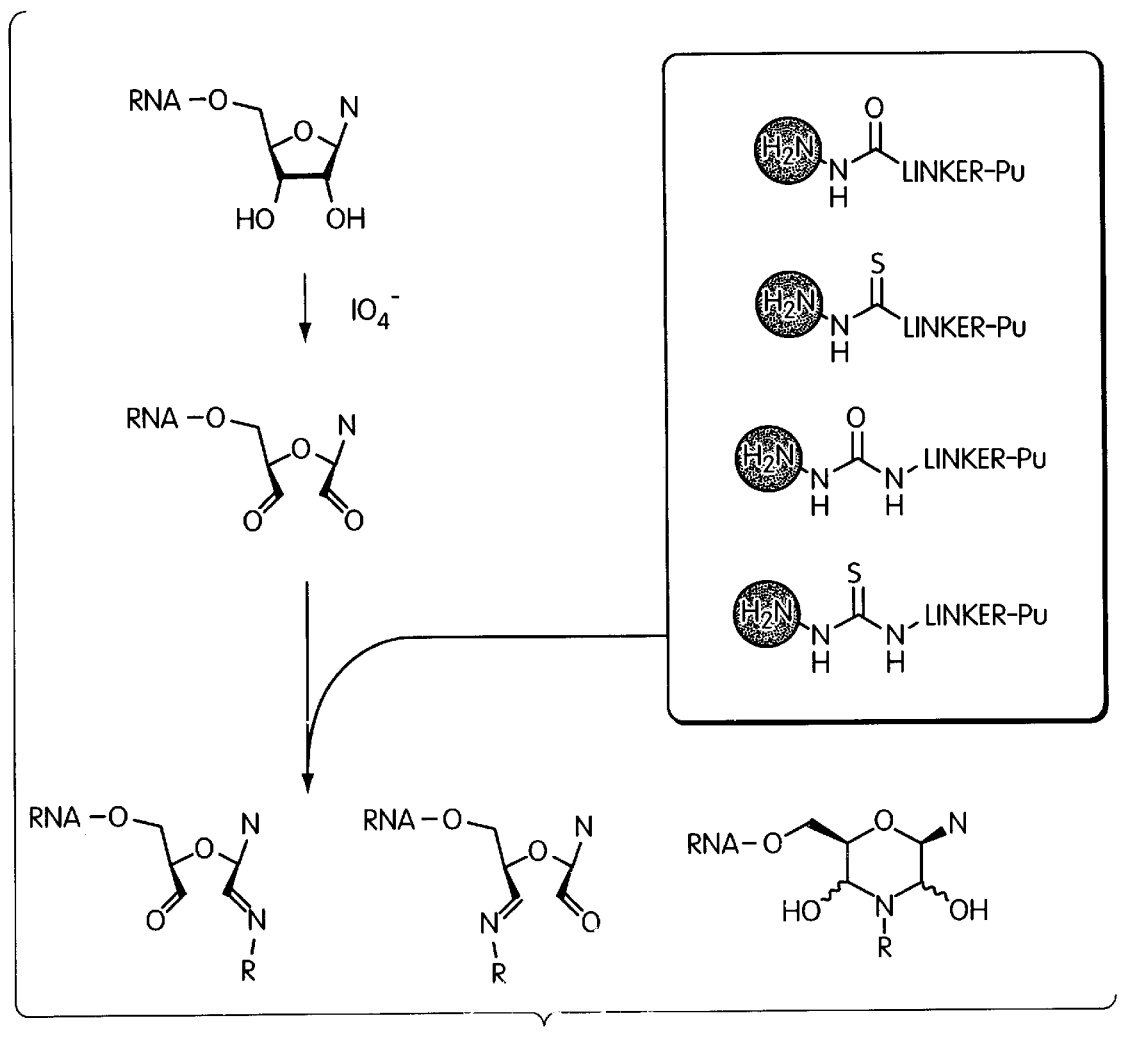
FIG. 3A is a schematic representation of exemplary steps involved in the 3' modification of an RNA through hydrazide and semicarbazone formation.
Figure 3B:
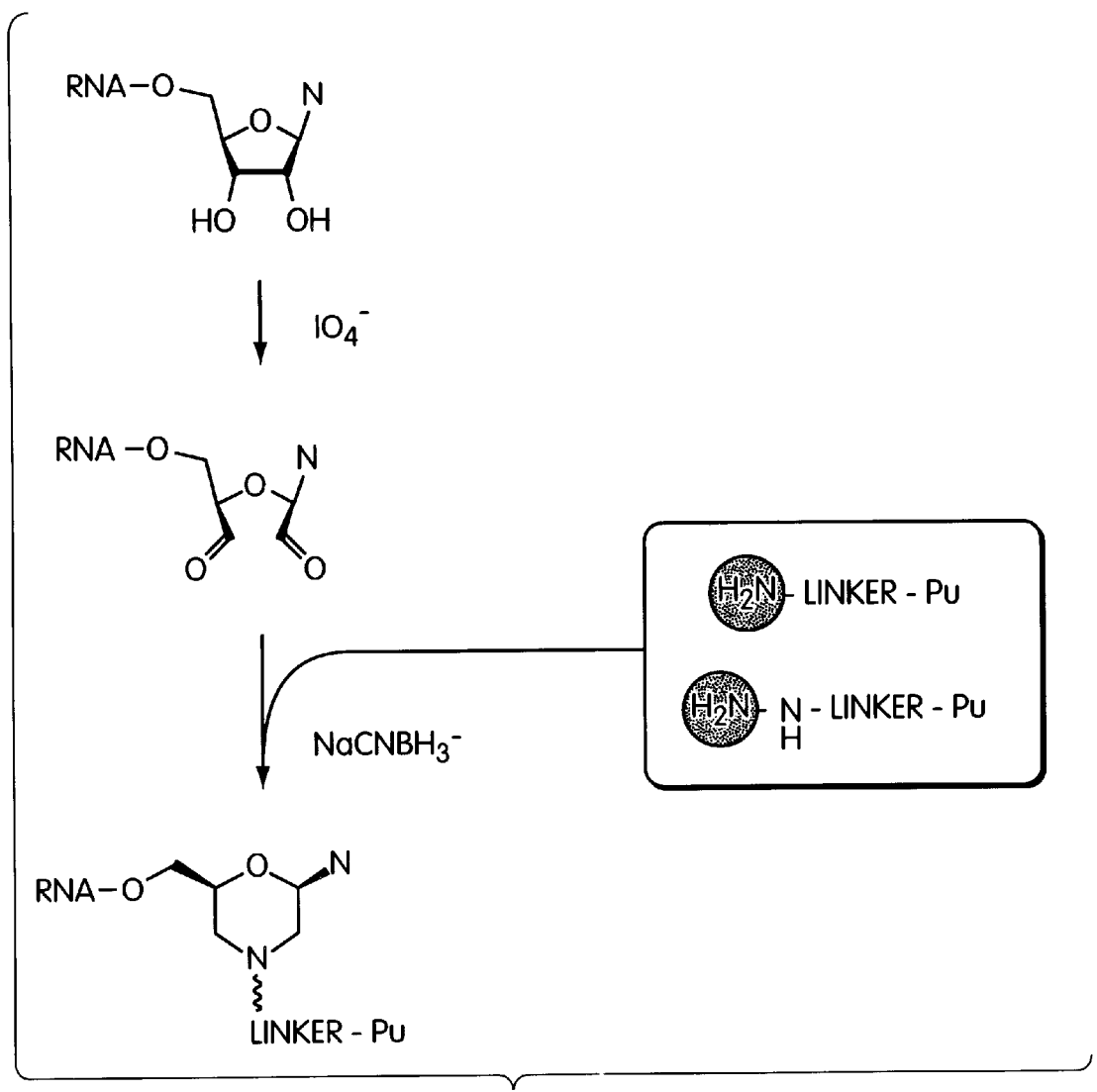
FIG. 3B is a schematic representation of exemplary steps involved in the 3' modification of an RNA through reductive amination.

Chemical Ligation Methods Involving Functionalization of the 3' End of an RNA Through $IO_4^-$ Oxidation Followed by Chemical Ligation According to the methods of the invention, a peptide acceptor can also be attached to an RNA molecule by functionalization of the 3' end of the RNA via $IO_4^-$ oxidation, followed by chemical ligation of the peptide acceptor to the RNA, as shown in FIG. 3A. The $IO_4^-$ oxidation is carried out as described below and according to the methods of Agrawal (*Methods in Molecular Biology*, Agrawal, ed., vol 26, Totowa: Humana Press, 1994, pages 93–120), Proudnikov and Mirzabekov, Nucleic Acids Res. 24:4535, 1996; Gosh et al., Anal. Biochem. 178:43,1989; Bauman et al., J. Histochem. Cytochem. 29:227, 1981; and Wu et al., Nucleic Acids Res. 24:3472, 1996). Since the $IO_4^-$ oxidation step strictly requires a 1,2-diol for reaction, only the terminal nucleotide is modified, leaving internal residues of the RNA molecule unaffected. The resulting dialdehyde can be subjected to a further reaction with various nucleophiles such as amines, hydrazines, carbo(thio)hydrazides, or (thio) semicarbazides, yielding Schiff base-like structures. These reactions are carried out as described, for example, in Agrawal (sra), Proudnikov and Mirzabekov (supra), Gosh et al. (supra), Bauman et al. (supra), and Wu et al. (supra). While the (thio)hydrazides and (thio)semicarbazones obtained after reaction with carbo(thio)hydrazides and (thio) semicarbazides, respectively, are fairly stable, the initial adducts containing amines or hydrazines usually require a subsequent reduction step, such as reductive amination, as shown in FIG. 3B and as described in Agrawal (supra), Proudnikov and Mirzabekov (supra), Gosh et al. (supra), Bauman et al. (supra), and Wu et al. (supra), to render the newly formed bonds stable toward hydrolysis.

Figure 4A:
FIGS. 4A–4D are a series of diagrams showing exemplary strategies for the chemical ligation of a functionalized puromycin linker to a functionalized RNA. One strategy is template-independent (FIG. 4A). Other strategies involve using external oligo templates to align the RNA and puromycin linker. In the strategies involving external oligo templates, the oligo template may hybridize to both the RNA and puromycin linker (FIG. 4B), or be attached to the puromycin linker and hybridize to the RNA (FIG. 4D). In addition, the functional group may be at the 5' end of (FIGS. 4B and 4C) or internal to (FIG. 4D) the puromycin linker.
Figure 4B:
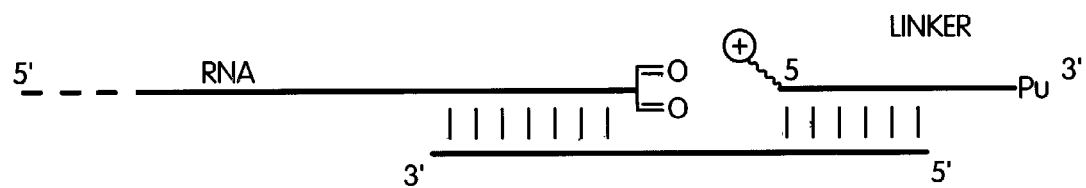
Figure 4C:
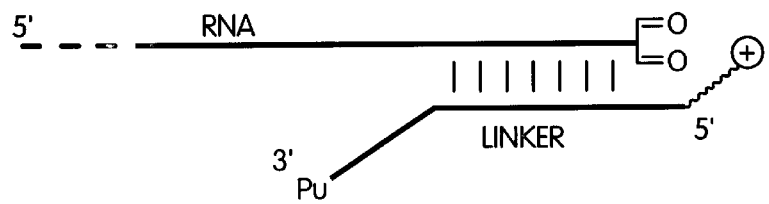
Figure 4D:
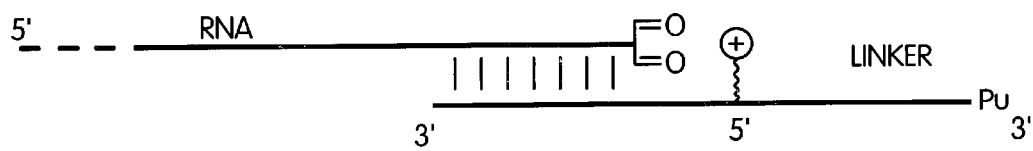

The above-described coupling reactions can be executed using a number of different strategies, as shown in FIGS. 4A–4D. For example, the ligation can be carried out in an external template-independent manner as shown in FIG. 4A. This strategy requires a large excess of modified peptide acceptor (for example, 100 to 1000-fold excess) to achieve successful ligation to the RNA molecule. To increase the efficiency of the RNA ligation, external template oligos may be used for substrate alignment as shown in FIG. 4B. Preferably, such oligos, which are complementary in sequence to the RNA and peptide acceptor linker sequences, are at least approximately ten nucleotides in length. Typically, this oligo will include at least approximately ten nucleotides which are complementary to the RNA molecule and approximately ten nucleotides which are complementary to the peptide acceptor linker. Alternatively, the reactive sites may be brought into close proximity by direct hybridization of linker and RNA domains as shown in FIGS. 4C–4D. Here, the extent of hybridizing sequence is at least ten to fifteen nucleotides.

A number of different constructs for the attachment of peptide acceptors to RNA via crosslink formation may be utilized. For example, one type of exemplary construct includes a peptide acceptor attached to a linker carrying a modification at its 5' end as shown in FIGS. 4A–4C. An alternative construct may comprise an internal functional group flanked by a hybridization domain on one side and a puromycin-linker portion on the other (FIG. 4D).

Figure 5:
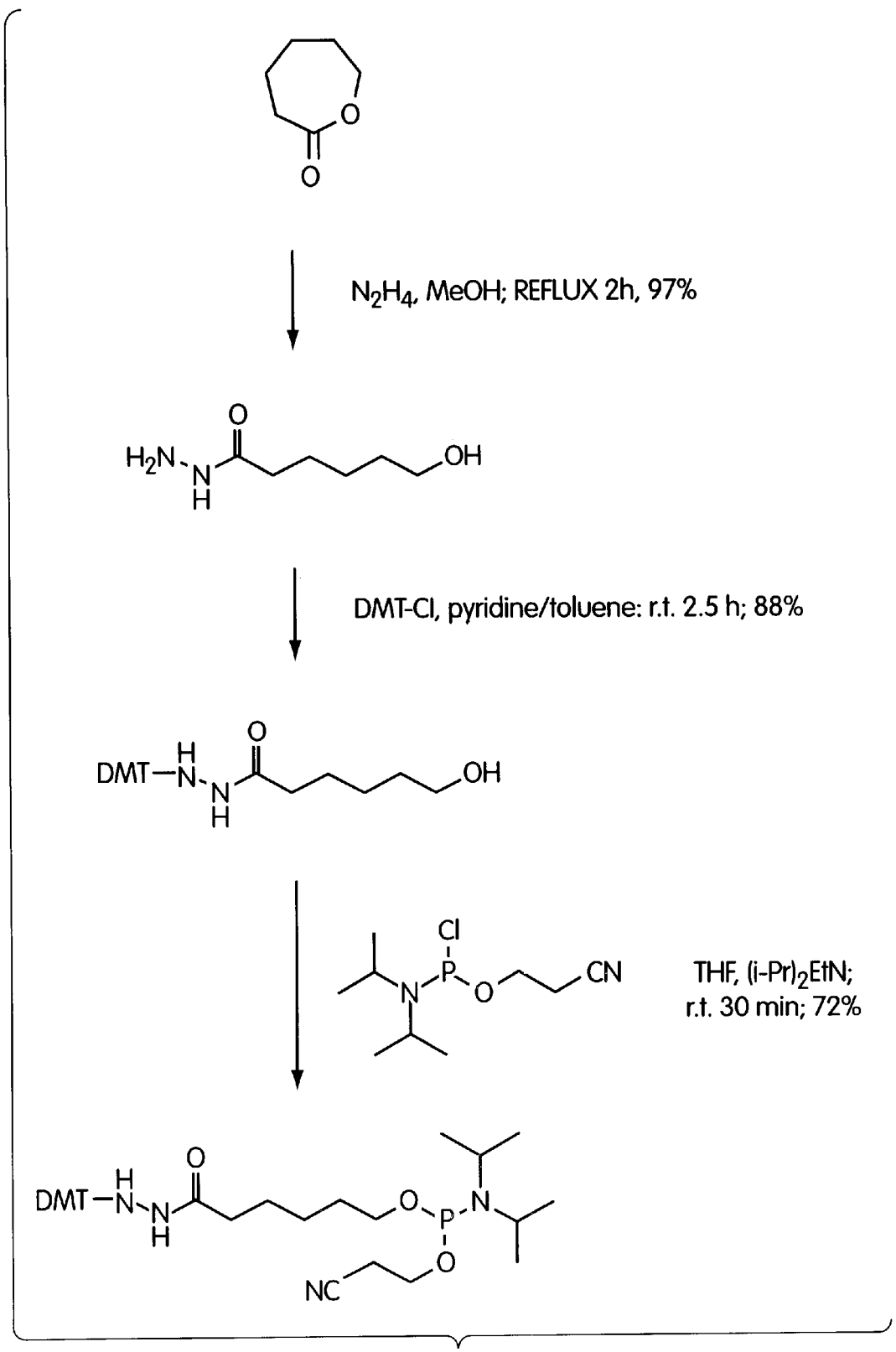
FIG. 5 is a schematic representation of exemplary steps involved in the synthesis of a fully protected carbohydrazide phosphoramidite for use in a modified puromycin linker.

The synthesis of these modified linkers involves standard automated DNA synthesis using commercially available phosphoramidites (Glen Research, Sterling, Va.) for assembling the main body of nucleotides or spacer moieties. The 3' puromycin may be introduced through the use of puromycin-CPG (Glen Research, Sterling, Va.) as a solid support for synthesis. The attachment of the reactive functional groups may be achieved using commercially available reagents such as amino terminus-modifiers (Glen Research, Sterling, Va.) or uni-link amino modifiers (Clontech, Palo Alto, Calif.). Other functional groups may be incorporated utilizing appropriate phosphoramidites. One exemplary method to generate a carbohydrazide phosphoramidite is described in FIG. 5. A carbohydrazide phosphoramidite was generated by combining a lactone with hydrazine and methanol and placing the reactants under reflux for 2 hours to produce a carbohydrazide moiety. The yield for this step of the synthesis was 97%. The resulting product was then reacted with the salt of a dimethoxytrityl group and pyridine/toluene at room temperature for 2.5 hours to yield a protected carbohydrazide moiety. The product yield for this step was 88%. This product was further reacted with a phosphoramidite moiety in the presence of tetrahydrofuran and diisopropylamine at room temperature for 30 minutes, which yielded (72%) a reaction product of a fully protected carbohydrazide phosphoramidite.

In addition, the reactivity of the peptide acceptor toward the $IO_4^-$ oxidized RNA may be further enhanced through introduction of multiple copies of reactive groups.

One exemplary ligation reaction was carried out as follows. One nmole of RNA, consisting of a transcript encoding a flag epitope and a strep tag, of the sequence: 5' G GGA CAA UUA CUA UUU ACA AUU ACA AUG GAC UAC AAG GAC GAU GAC GAU AAG GGC GGC UGG UCC CAC CCC CAG UUC GAG AAG GCA UCC GCU (SEQ ID NO:1) was combined with 20 μl of 500 mM NaOAc (pH 5.2), 101 μl of 5 mM NaIO$_4$, and brought up to a final volume of 100 μl with water. The reaction mixture was incubated for 15 minutes at room temperature. Next, 10 μl of 10 mM Na$_2$SO$_3$ was added, and the reaction mixture was incubated again for 15 minutes at room temperature. Forty μl of 1 M phosphate buffer (pH 8.0), 1.5 nmole of the peptide acceptor linker Uni-A1/8, having the sequence: 5' X CGC GGA TGC AAA AAA AAA AAA AAA AAA AAA AAA AAA CC Pu (SEQ ID NO:2) (where X is a Uni-link amino modifier [Clontech], and Pu is Puromycin-CPG [Glen Research]), and 20 μl of NaCNBH$_3$ were added to the reaction mixture. The mixture was then incubated for 18 hours at room temperature, precipitated, purified on a 6% TBE-Urea gel, and crush-soaked overnight to obtain the RNA-protein fusion molecule. This reaction yielded 230 pmole of product.

EXAMPLE 4

Figure 6:
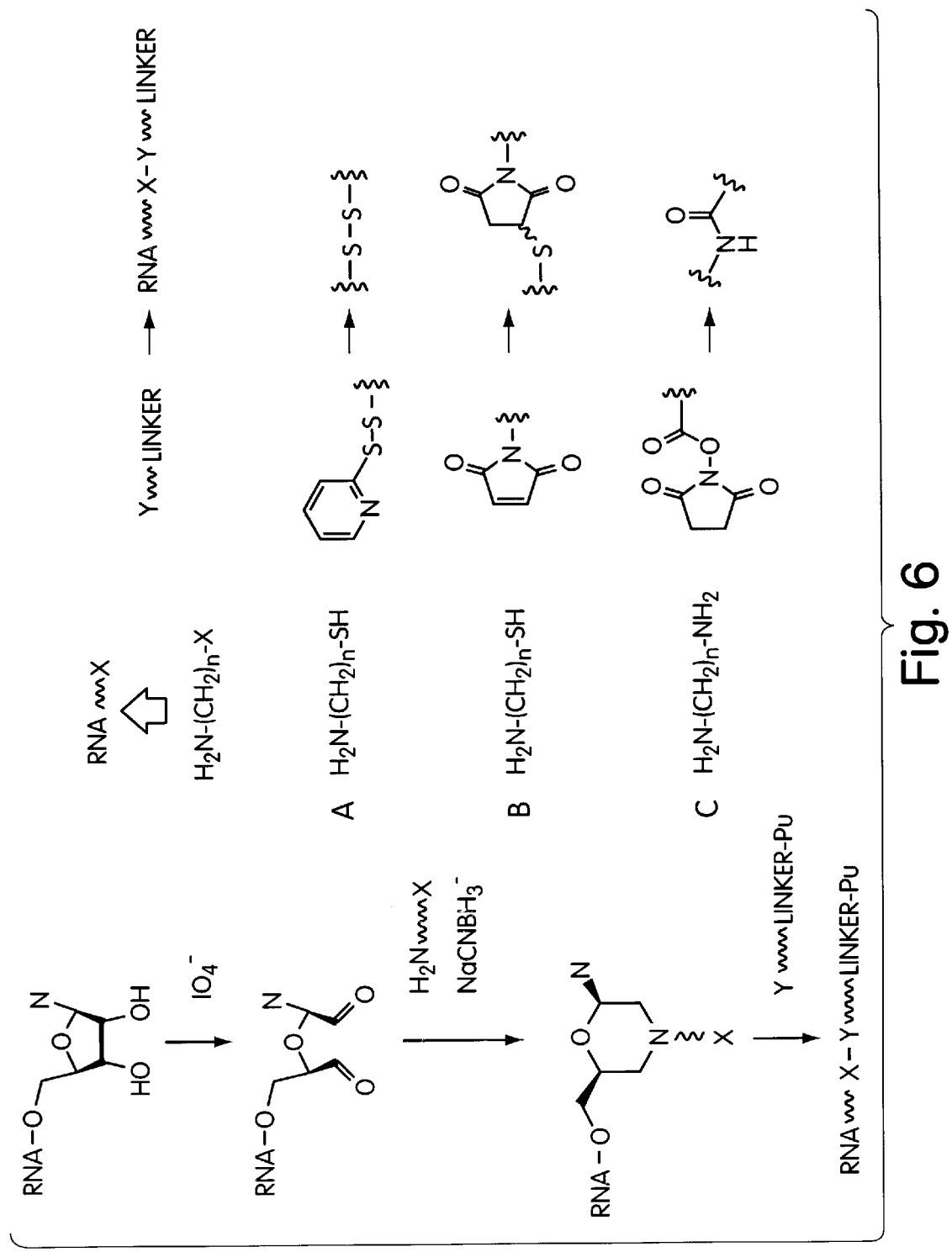
FIG. 6 is a schematic representation of exemplary steps involved in the ligation of a peptide acceptor linker to an RNA by attaching a functional group to the 3' end of the RNA followed by chemical ligation. The functional group can then react with a suitably modified linker molecule to covalently bond the RNA and puromycin linker, through a thiol (A), maleimide (B), or amine group (C).

Chemical Ligation Methods Involving Attachment of Functional Groups to the 3' End of an RNA Molecule Followed by Chemical Ligation A peptide acceptor can also be affixed to an RNA molecule by attaching a functional group to the 3' end of the RNA followed by chemical ligation, as shown in FIG. 6. In a variation of the process described above, reductive amination and related reactions are used to attach functional groups to the 3' terminus of an RNA. These newly introduced groups then react further with suitably modified linkers on the peptide acceptor, leading to covalent bond formation between the RNA and peptide acceptor. Exemplary reactive groups include thiols (for disulfide formation or reactions with thiolphilic reagents such as pyridyl disulfides; FIG. 6, Reaction A) or maleimides (FIG. 6, Reaction B).

Other possible reactive groups for the functionalization of the 3' end of an RNA followed by attachment of a peptide acceptor are amines. For example, N-hydroxysuccinimide-esters (NHS-esters) can be generated on 5' amino-modified linkers of the peptide acceptor by reaction with disuccinimidyl glutarate (DSG) or related reagents as described in Cox et al. (J. Immunol. 145:1719, 1990) and Pierce catalog (Pierce, Rockford, Ill.; FIG. 6, Reaction C). This modified linker can then be reacted with the amino functional group of the modified RNA.

This type of ligation reaction may be carried out in either an external template-independent or -dependent manner as described above, using the same general approaches.

EXAMPLE 5

Chemical Ligation Methods Involving Photochemical Methods

A peptide acceptor can also be attached to an RNA molecule using photochemical methods as shown in FIGS. 7A–7H. Peptide acceptor linker molecules that carry psoralen groups allow the introduction of crosslinks to complementary RNA strands upon irradiation with long wave UV-light. This technique may be carried out generally as described in Pieles and Englisch, (Nucleic Acids Res. 17:285, 1989) and Godard et al. (Nucleic Acids Res. 22:4789, 1994). Attachment of the psoralen moiety to the 5' terminus of the linker region of the peptide acceptor can be accomplished using commercially available psoralen amidites, 2'-OMe-RNA phosphoramidites, psoralen C6 phosphoramidites, and triethylene glycol (TEG) phosphoramidites (Glen Research, Sterling, Va.) on a standard DNA synthesizer.

In one exemplary approach, this method was carried out as follows. One nmole of RNA consisting of an RNA transcript encoding a flag epitope, a strep tag, and a photochemical target site of the sequence: 5' G GGA CAA UUA CUA UUU ACA AUU ACA AUG GAC UAC AAG GAC GAU GAC GAU AAG GGC GGC UGG UCC CAC CCC CAG UUC GAG AAG AAC GGC UAU A (SEQ ID NO:3), 1.2 nmole of Photolinker 30/10 consisting of the sequence: 5' Pso TAG CCG TTC T AAA AAA AAA AAA AAA AAA AAA AAA AAA CC Pu (SEQ ID NO:4) (where Pso is a psoralen C2 amidite [Glen Research], and Pu is Puromycin-CPG [Glen Research]), synthesized according to standard manufacturer protocols, or 30/15 consisting of the sequence: 5' Pso TAG CCG TTC TTC TCG AAA AAA AAA AAA AAA AAA AAA AAA CC Pu (SEQ ID NO:5) (where Pso is a psoralen C2 amidite, and Pu is Puromycin-CPG), 10×buffer (250 mM Tris pH 7.0; 1 M NaCl), and water (bringing the final volume to 360 μl) were combined and heated to 80° C. for 2 minutes. The reaction mixture was then slowly cooled to room temperature. The reaction mixture was next irradiated for 15 minutes at 0° C. with λ greater than 310 nm using a 450 W immersion lamp (medium pressure; ACE Glass, cat. no. 7825–34), equipped with a Pyrex absorption sleeve (ACE Glass, cat. no. 7835-44) in a Quartz immersion well (ACE Glass, cat. no.

7854-25), with the sample in a microcentrifuge tube strapped to the immersion well, and cooled in ice-water. The sample was then precipitated with 40 µl of 3 M NaOAc and 1000 µl of ethanol, and resuspended in 75 µl of water. Next, 75 µl of 2×loading buffer (Novex) was added to the sample, and the sample was purified on a precast 6% TBE-Urea gel (Novex). The product was recovered using a crush and soak method (0.3 M NaOAc, overnight at room temperature) followed by ethanol precipitation. This photocrosslinking method yielded 272 pmole of RNA-protein fusion product using Photolinker 10/30, and 227 pmole using Photolinker 15/30.

For this photocrosslinking method of chemical ligation, various parameters of the reaction were evaluated. First, the salt dependence of the photocrosslink formation was tested. A set of crosslinking experiments with buffers containing 100–1000 mM NaCl were performed. No difference in ligation efficiencies were observed between the various reactions. In addition, a change of the RNA target sequence to: 5' . . . GAC UAC AAG GAC GAG GCA UCC GCU CUU UCA CUA UA (SEQ ID NO:6) (with the underlined sequence being a target for the psoralen linker) gave significantly reduced product yields (15 to 20% reduced), indicating that the RNA target sequence was important. Next it was determined that the product yield could be increased by the repeated replacement of psoralen linkers that had been inactivated during the course of the reaction. This experiment was carried out as follows. The RNA, linker, and 10×buffer were combined and heated to 80° C. for 2 minutes. The reaction mixture was then slowly cooled to room temperature and irradiated as described above. Then an additional 1 nmole of linker and 1 µl of buffer were added. The linker annealed to the RNA and was then irradiated. This process was repeated, by adding 2 nmole of linker and 2 µl of buffer and irradiating. This procedure allowed an increased product yield from 20% to greater than 40% for certain sequences.

The performance of the ligation products generated by photochemical crosslinking methods was also evaluated. In experiments with linkers of different lengths (psoralen plus 15 base pairs of target hybridization domain plus dA$_n$CCPu [where n=7, 12, 17, or 22]) the following observations were made. Long linkers gave the highest RNA-protein fusion yields under high salt conditions (500 mM KCl plus 50 mM MgCl$_2$). In buffers with reduced salt (250 mM KCl plus 10 mM MgCl$_2$, or 250 mM KCl), the short linkers produced higher yields than the longer ones, but the overall yields were generally lower. In general, yields seem to be comparable to those obtained with enzymatically ligated RNA templates.

In other exemplary methods, various mRNAs and puromycin linkers were synthesized such that the peptide acceptor was positioned at the 3' end of the linker. The linkers were annealed to the target mRNAs and evaluated for their efficiency in forming mRNA-protein fusions molecules through in vitro translation techniques. The effect of the linker length and composition on fusion molecule yield was also determined.

Figure 7A:
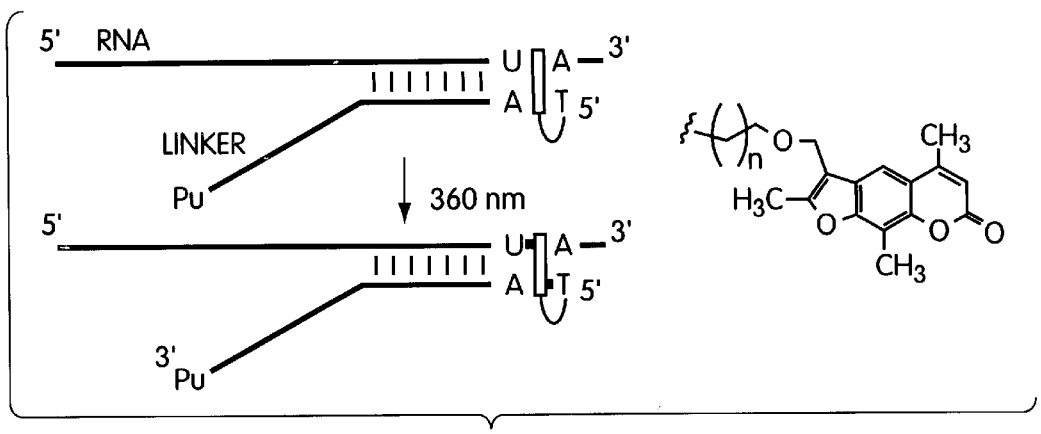
FIGS. 7A–7C are a series of schematic representations of exemplary steps involved in the ligation of a peptide acceptor to an RNA using photocrosslinking. In this general method, a psoralen moiety attached to the puromycin linker crosslinks the puromycin linker to the RNA upon exposure to UV irradiation. The psoralen moiety can be at the 5' end of (FIG. 7A), internal to (FIG. 7B), or at the 3' end of (FIG. 7C) the puromycin linker.
Figure 7B:
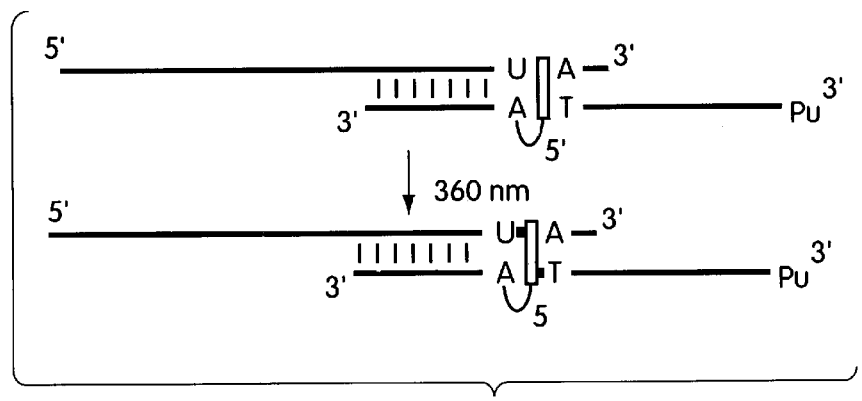
Figure 7C:
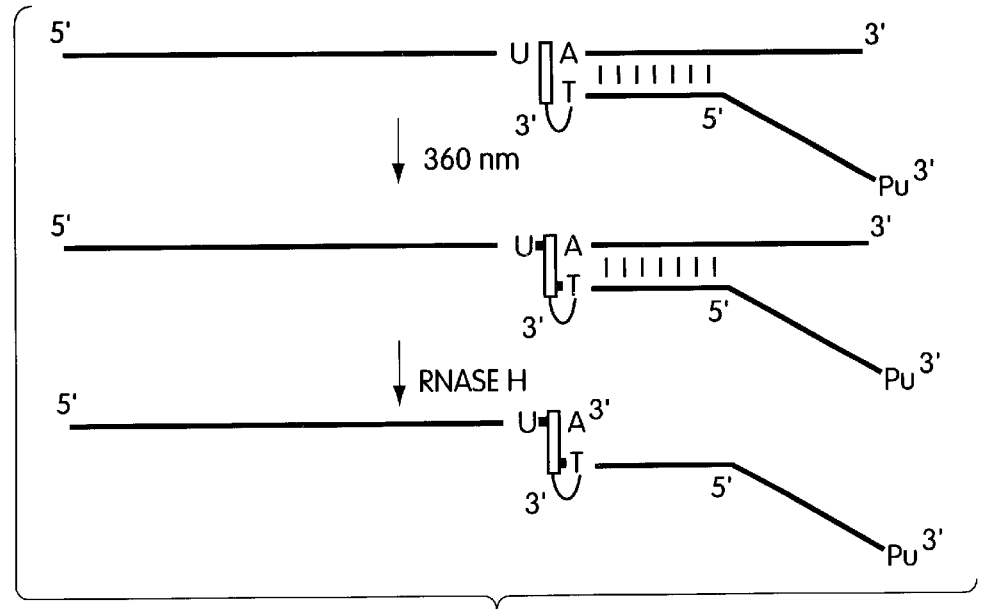
Figure 7D:
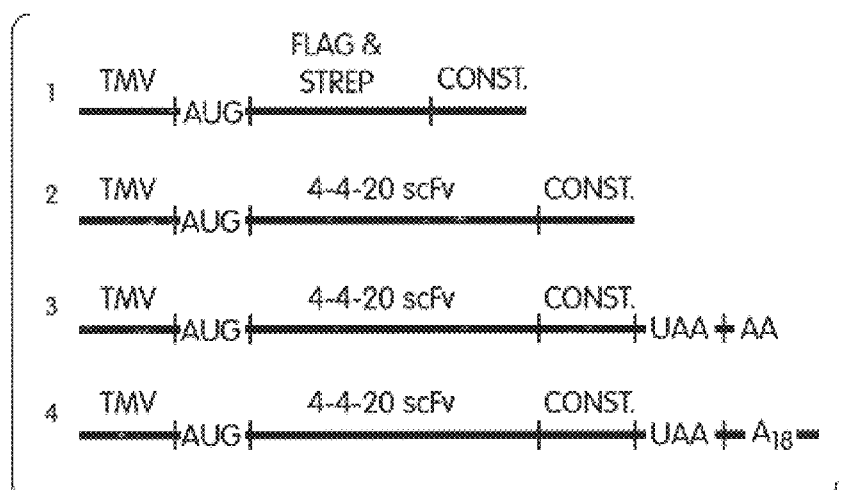
FIG. 7D is a schematic representation of mRNAs used for photo-crosslink formation.

FIG. 7D illustrates the design of the mRNAs used in the crosslinking reactions. Each of the RNA molecules contained a portion of the tobacco mosaic virus 5'-UTR (TMV) with good initiation codon context (Gallie et al., Nucleic Acids Res., 16:883–93, 1988; and Kozak, Microbiol. Rev., 47:1–45, 1983), and a translation initiation codon (AUG). All mRNAs also carried a 3'-terminal ten nucleotide linker hybridization sequence 5'-GCAUCCGCUAUU (SEQ ID NO: 8) coding for the amino acid sequence ASA, and ending with the dinucleotide sequence 5'-UA for psoralen photocrosslinking (const.), as described by Sinden and Hagerman (Biochemistry, 23:6299–6303, 198) and Gamper et al., (Photochem. Photobiol., 40:29–34, 1984). In addition one mRNA (mRNA 1) contained a Flag epitope, DYKDDDDK (SEQ ID NO: 9) (Hopp et al., Biotechnology, 6:1205–1210, 1988) followed by a Strep-Tag II sequence, WSHPQFEK (Schmidt et al., J. Mol. Biol., 255:753–66, 1996). Other MRNA molecules (mRNAs 2, 3, and 4) contained a 4-4-20 scFv, anti-fluorescein single chain antibody template, as described by Bedzyk et al. (J. Biol. Chem., 265:18615–20, 1990) and Mallender et al. (J. Biol. Chem., 271:5338–46, 1996). In addition, mRNAs 3 and 4 contained a downstream stop codon (UAA) to induce mRNA release from the ribosome after translation of residual un-crosslinked template (vide infra). A poly-A tail was also attached to mRNA 4 for purification by oligo-dT.

The mRNAs used in these studies (FIG. 7D) were prepared by T7 RNA polymerase run off-transcription (Megashortscript Transcription Kit, Ambion, Tex.) of PCR DNA templates, according to the methods of Milligan et al. (Nucleic Acids Res., 15:8783–8798, 1987). After transcription, all RNAs were purified by electrophoresis on 6% TBE-urea polyacrylamide gels (Novex, Calif.). The product bands were visualized by UV-shadowing, excised, crushed, and soaked overnight in 0.3 M NaOAc. Following ethanol precipitation, the RNAs were resuspended and stored in H$_2$O. Radiolabeled RNA was synthesized according to the same procedure by including [α-$^{32}$p] UTP (Amersham, Ill.) in the transcription buffer.

The puromycin-linkers used in these studies (FIG. 7E) were prepared using an Expedite Synthesizer Model 8909 (PerSeptive Biosystems, Mass.), using conventional solid-support phosphoramidite chemistry. Puromycin-CPG, DNA phosphoramidites, 2'-OMe-RNA phosphoramidites, psoralen C6 phosphoramidite, and triethylene glycol (TEG) phosphoramidites (spacer 9) were used according to the recommended protocols (Glen Research). A psoralen moiety was attached through a C6 alkyl chain to the 5'-phosphate of the linker. Flexible triethyleneglycol phosphate (TEG) spacers and polynucleotide sequences of various lengths were used to tether 5'-dCdC-puromycin to the 3'-end (see the table in FIG. 7E). The linker hybridization sequence was prepared from 2'-OMe-RNA phosphoramidites to enhance the pairing stability of the stem structure (Inoue et al., Nucleic Acids Res., 15:6131–6148, 1987; and Majlessi et al., Nucleic Acids Res., 26:2224–2229, 1998). Following deprotection in concentrated ammonium hydroxide for 8 hours at 55° C., the linkers were purified by reversed phase HPLC on a C18 Spheri-5 column (Perkin Elmer, Calif.) with 50 mM triethylammonium acetate in 5% v/v acetonitrile as buffer A, and 50 mM triethylammonium acetate in 70% v/v acetonitrile as buffer B and with a flow rate of 1.5 ml/min. A linear gradient of 15–60% buffer B over 45 minutes was used for elution. After drying, the linkers were resuspended and stored in H$_2$O.

Figure 7E:
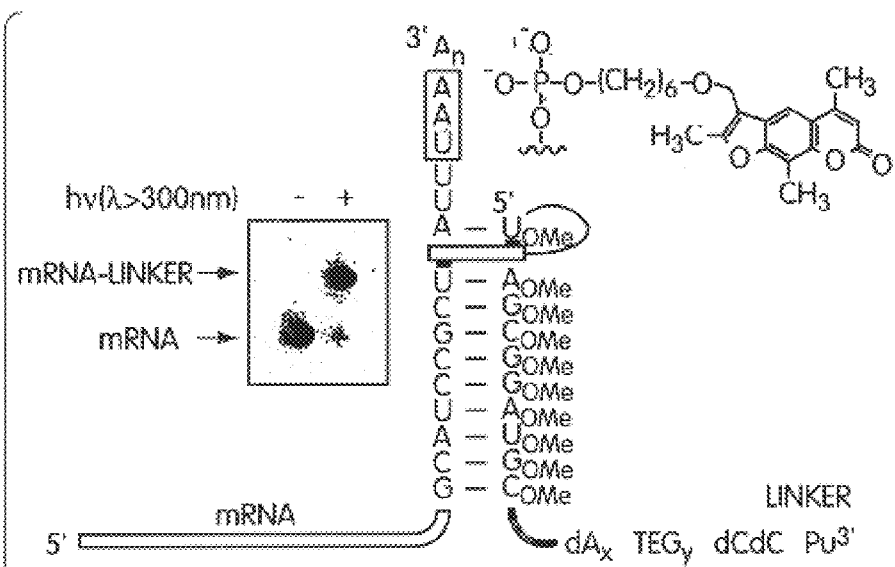
FIG. 7E is a schematic representation of a duplex formed between the constant 3'-sequence of the mRNA (const. region of the mRNAs of FIG. 7D)) and the photolinker showing the putative psoralen intercalation site. Also shown is the structure of psoralen, which was attached through a C6 alkyl chain to the 5'-phosphate of the linker. The variables x and y determine the number of dA-nucleotides and triethyleneglycol-units (TEG) in the linker, respectively. The autoradiograph on the left depicts the gel-electrophoretic analysis of the photo-crosslinking reaction between mRNA 1 and linker B.

The linkers (5 µM) were annealed to the target mRNAs (2.5µM) in 25 mM Tris HCl buffer, pH 7, and 100 mM NaCl by heating to 85° C. for 30 seconds, followed by cooling to 4° C. over a period of 5 minutes. The reaction mixture was irradiated for 15 minutes at room temperature in borosilicate glass vials (Kimble/Kontes, N.J.), using a handheld multi-wavelength UV lamp model UVGL-25 (UVP, Calif.) set to a long wave (wavelength λ>300 nm). The product mixture of the photocrosslinking reaction between radiolabeled mRNA 1 and linker B was analyzed on a denaturing 6% TBE-Urea gel (Novex) and visualized on a phosporimaging system (Molecular Dynamics, Calif.) (FIG. 7E). These photocrosslink product mixtures generally contained <20% unreacted and >80% photocrosslinked mRNA, and were used directly for in vitro translation and subsequent mRNA-protein fusion formation without further purification. For the longer mRNA substrates 2, 3, and 4 (>800 nucleotides), the relative size difference between mRNA and crosslinked mRNA became too small to be separated on a gel. In these cases, the crude photo-crosslinking reaction mixtures were directly added to the lysate for fusion formation, without further purification.

Translation and fusion formation of the mRNA fusion molecules were first tested using mRNA 2 in the following experiments. In vitro translation reactions were performed using rabbit reticulocyte lysates (Ambion) for 30 minutes at 30° C. The reactions contained 100 pmole photo-crosslinked mRNA (see above), 10 mM creatine phosphate, 150 mM KOAc, 0.5 mM $MgCl_2$, 0.1 mM of each amino acid except methionine, 150 $\mu$uCi of [$^{35}$S] methionine (Amersham), and 67% v/v of lysate in a total volume of 300 $\mu$l. mRNA-protein fusion formation was promoted by the addition of KCl and $MgCl_2$ to the final concentrations of 590 mM and 50 mM, respectively, in a 500 $\mu$l volume, according to the methods of Roberts & Szostak and Szostak et al. (supra). Incubation was continued for another 60 minutes at 20° C. Varying concentrations of KCl and $MgCl_2$ were also tested to explore salt dependence on fusion formation.

The in vitro translation products were isolated by diluting the lysate into 10 ml of binding buffer (100 mM Tris HCl, pH 8.0, 10 mM EDTA, 1 M NaCl, 0.25% v/v Triton X-100) and by adding to the mixture 10 mg of oligo-dT cellulose type 7 (Pharmacia, N.J.). The samples were rotated for 60 minutes at 4° C. The solid support was then washed with 5 ml of ice-cold binding buffer, followed by elution with 100 $\mu$l aliquots of deionized $H_2O$. The amount of mRNA-protein fusion isolated was determined by scintillation counting of the incorporated [$^{35}$S] methionine. The product was analyzed by electrophoresis on 4–12% NuPage gels using MES running buffer (Novex). The gels were dried after extensive washing to remove excess [$^{35}$S] methionine, and bands were visualized on a phosphorimager system (Molecular Dynamics).

Figure 7F:
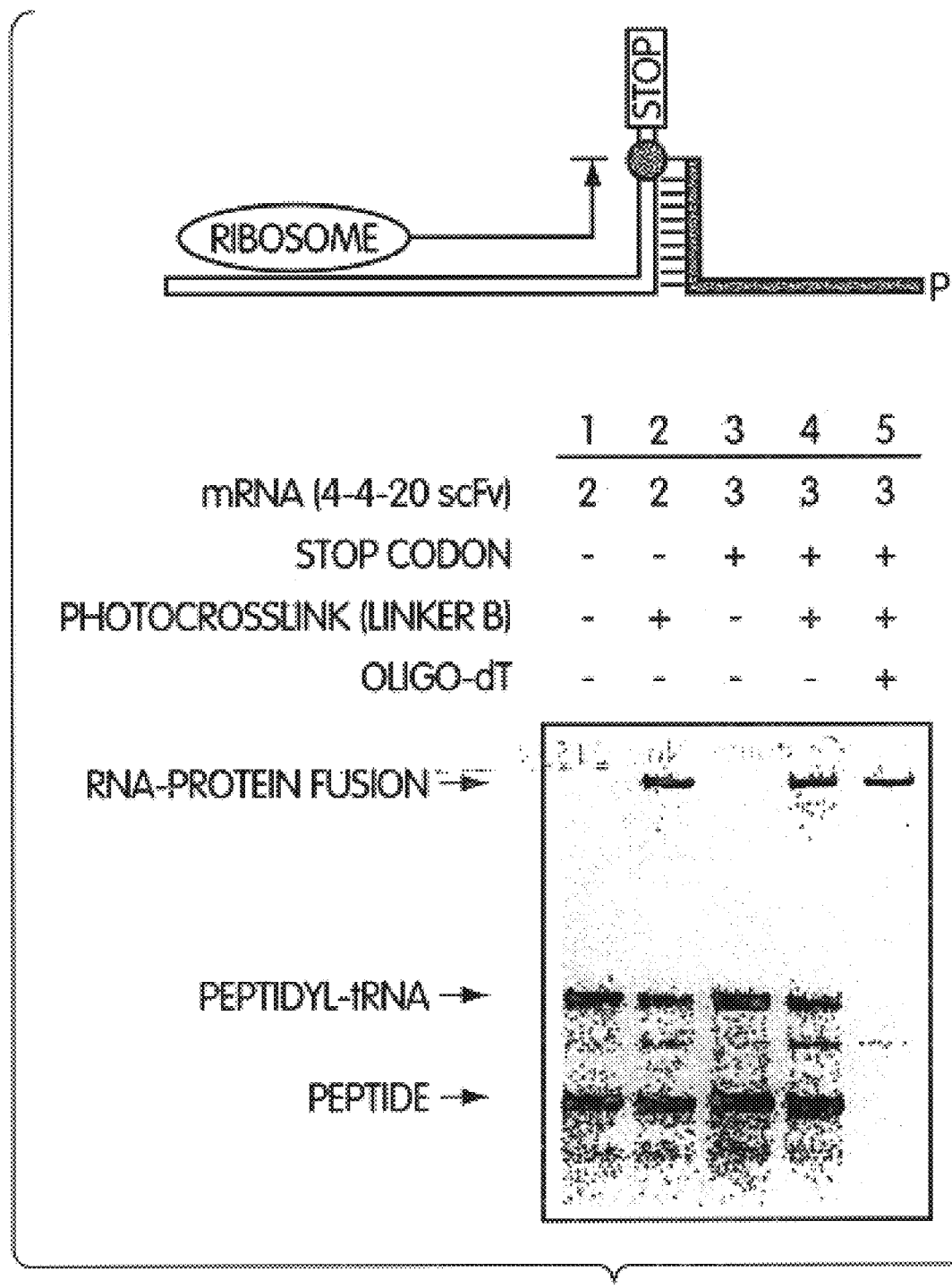
FIG. 7F is an image of a gel illustrating in vitro translation and fusion formation. Protein synthesis from mRNA template 2 and template 3 is shown in lanes 1 and 3, respectively. Translation of mRNA templates photo-crosslinked to linker B produced mRNA-protein fusions (lanes 2 and 4). Template 3 carries a stop codon following the linker crosslink-site. Lane 5 shows the fusion product after purification on oligo-dT cellulose. A schematic representation of fusion formation using an mRNA molecule containing a stop codon is depicted above the image of the gel.

Gel analysis showed two bands that corresponded to the peptidyl-tRNA and the free peptide (FIG. 7F, lane 1). When translation was carried out with photo-crosslinked mRNA 2, a third and slower migrating band appeared, thus indicating successful mRNA-protein fusion formation (FIG. 7F, lane 2). Increased yields of free protein and fusion (approximately 20% more) were obtained with mRNA 3, which was identical in coding sequence to mRNA 2, but carried a stop-codon downstream of the photo-crosslink site (FIG. 7F, lanes 3 and 4). Relative band intensities indicated that 30% of the total amount of synthesized protein was converted into mRNA-protein fusion (FIG. 7F, lane 4).

An mRNA-scFv fusion molecule, prepared from mRNA 4 of FIG. 7E, was purified by binding of the $A_{18}$ linker regions to oligo-dT cellulose, followed by washing with binding buffer, according to the methods of Roberts & Szostak and Szostak et al. (supra) (FIG. 7E, lane 5). The fusion product could be isolated with a 1.3% yield based on the amount of photo-crosslinked input MRNA. Physical properties (gel mobility, binding to oligo-dT cellulose, selective peptide binding to affinity reagents) of the fusions prepared from photo-crosslinked mRNA were found to be identical to those of the fusion product obtained from enzymatically ligated mRNA templates.

In order to confirm the composition of the peptide portion of the fusion molecules, fusions prepared from the mRNA template 1 crosslinked to linker B of FIG. 7E, encoding the Flag and Strep-Tag II epitope, were tested for protein binding. A solution of 10 $\mu$l of $^{35}$S-labeled mRNA-peptide fusion (prepared from mRNA 1 with linker B) was added to 20 $\mu$l of Anti-Flag M2 Affinity Gel (Sigma, MO) in 300 l of buffer containing 50 mM Tris HCl, pH 7.4, 1% NP 40, 150 mM NaCl, 1 mM EDTA, 1 mM $Na_3VO_4$, and 1 mM NaF. A second precipitation experiment was carried out by adding the same fusion product to 20 $\mu$l of StrepTactin Sepharose (Genosys, Tex.) in 300 gl of buffer containing 100 mM Tris-HCl, pH 7. 1, 1 mM EDTA, and 0.5 mg/ml yeast tRNA. Both precipitation mixtures were processed in parallel under identical conditions: The mixtures were rotated for 1 hour at 4° C. and then transferred onto an Ultrafree-MC filter unit (0.45 gm; Millipore, Mass.). The buffer was removed by centrifugation, and the residue washed with 5×300 $\mu$l of ice-cold buffer. The residues were analyzed by scintillation counting, and fusion binding was determined to be 54% and 62% for the Anti-Flag M2 matrix and the StrepTactin matrix, respectively. A control reaction with protein-A agarose (Sigma) showed no detectable binding to the matrix.

Figure 7G:
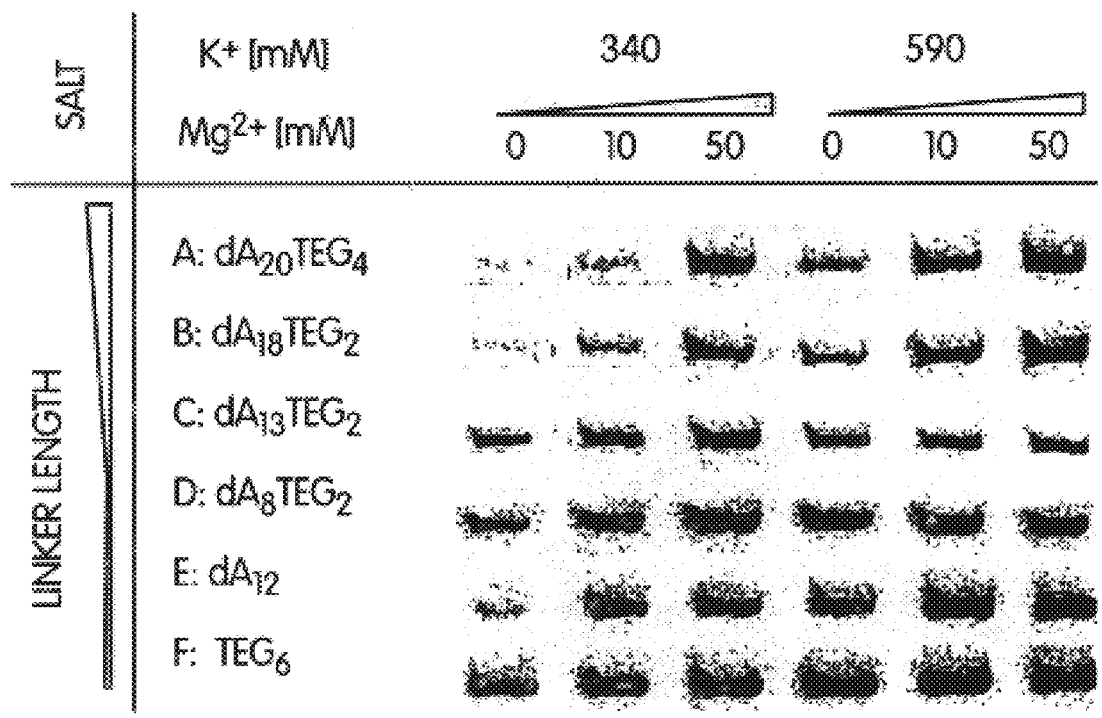
FIG. 7G is an image of a gel illustrating the dependence of mRNA-protein fusion molecule yield on linker composition and on salt concentration.
Figure 7H:
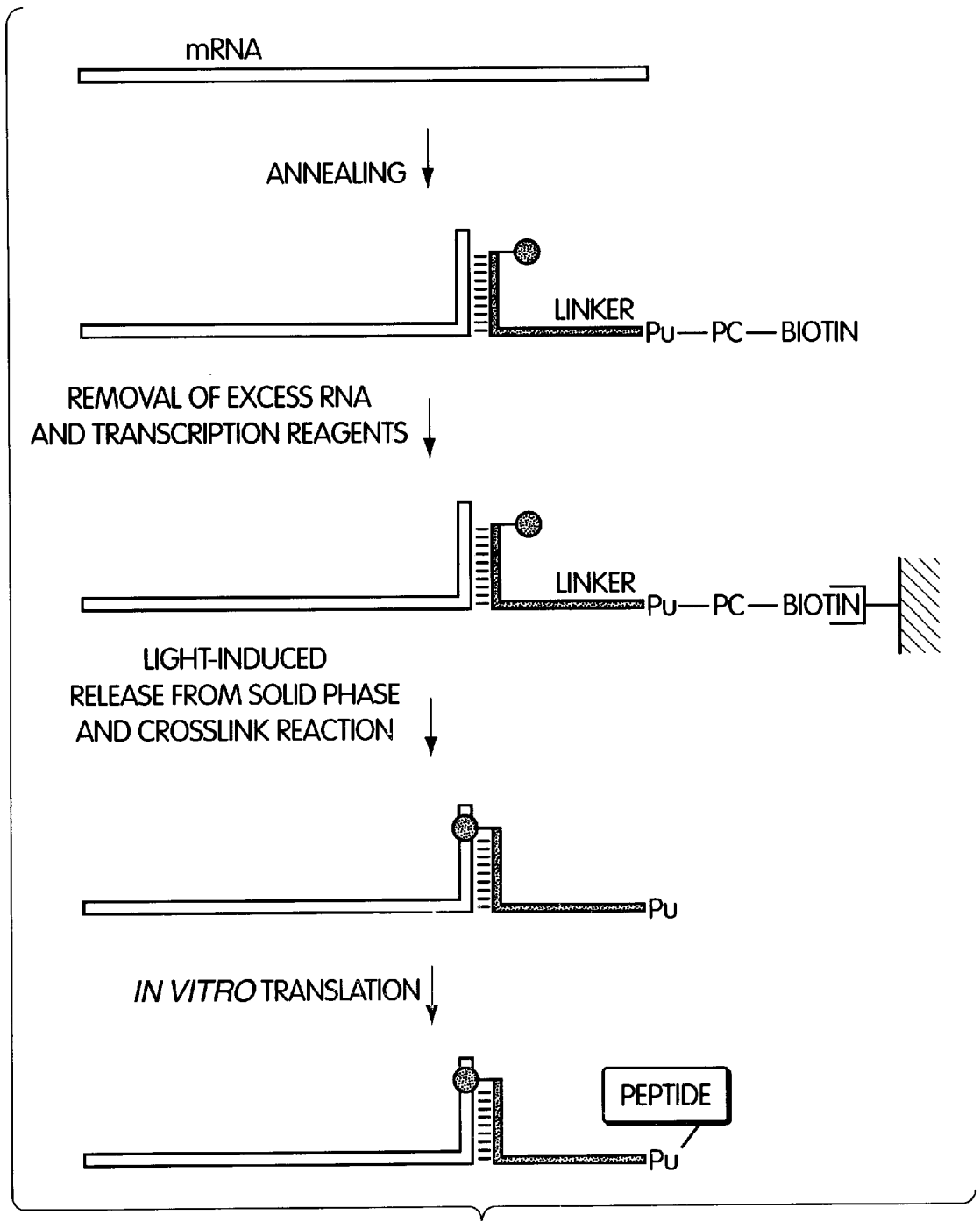
FIG. 7H is a schematic representation of the steps involved in the ligation of mRNA to photocleavable biotin-based hybridized linkers and their subsequent fusion formation.

To test the effect of linker length and composition on fusion formation in the presence of various salt concentrations, mRNA 3 was photo-crosslinked to linkers A–F of FIG. 7E and each template was subsequently tested for fusion formation (FIG. 7G). After incubation for 30 minutes at 30° C., the samples were divided into aliquots, to which varying amounts of KCl and $MgCl_2$ were added. The samples were incubated for another 60 minutes at 20° C.; then, the fusion product was analyzed by gel-electrophoresis. The highest mRNA-protein fusion yields were obtained with the long linkers A and B (40 and 35 nucleotides, respectively) under high salt conditions. A lower salt concentration resulted in a significant drop in fusion formation with the linkers A and B. On the other hand, fusion yields for the shorter linkers C to F were less salt dependent. In addition, the fusion molecule yield generally increased with the number of flexible TEG spacers. Analysis of the crude mRNA-protein fusion molecule lysates revealed that up to 45% of the total protein was present as mRNA-protein fusion. Because linker F lacked the oligo-dA track needed for oligo-dT purification, mRNA 4 was prepared with an $A_{18}$ (SEC ID NO: 24) stretch at its 3'-end, which allowed fusion purification on oligo-dT cellulose.

In an alternative to the above techniques which involve attachment of psoralen to the linker 5' end, the psoralen moiety may also be incorporated at an internal position of the linker region of the peptide acceptor, as shown in FIG. 7B, and as described in Pieles et al. (Nucleic Acids Res. 17:8967, 1989), or by incorporation of a branched phosphoramidite (Clontech, Palo Alto, Calif.) within the linker sequence, followed by addition of a psoralen phosphoramidite (Glen Research, Sterling, Va.). For example, the psoralen moiety may be crosslinked to the RNA through a branched linker, as described in U.S. Ser. No. 09/453,190, incorporated herein by reference.

In one exemplary approach, a linker with the sequence 5' cgt agg cga gaa agt gat X AAA AAA AAA AAA AAA AAA AAA AAA AAA CC Pu (SEC ID NO: 10) (where Pu is Puromycin-CPG [Glen Research]; C and A are standard 3'-amidites [Glen Research]; a, t, c, and g are 5'-phosphoramidites [Glen Research]; and X is an asymmetric branching amidite [Clontech]) has been synthesized according to standard manufacturer protocols, followed by selective deprotection of the branching point X (according to the instructions of Clontech) and subsequent coupling of a psoralen C6 amidite (Glen Research). This linker was then photocrosslinked to an RNA with the target sequence 5' . . . GCA UCC GCU CUU UCA CUA UA (SEQ ID NO: 11) using the photocrosslinking techniques described above. This RNA-linker construct was then successfully used for the synthesis of RNA-protein fusions.

In yet another alternative, a linker containing a psoralen attached to the 3' end of the target hybridization domain may also be constructed (FIG. 7C). In this method, the 5' end of the psoralen-containing linker is extended by another linker, that after reversal of strand orientation, terminates with a 3' puromycin. A subsequent digestion of the RNA target domain with RNase H is optional and will increase the flexibility of the linker construct. In addition, this approach allows the attachment of the linker at internal positions of much longer RNA molecules, and the untranslated region downstream from the linker site is then clipped off before translation and RNA-protein fusion formation.

In one exemplary approach to this method, a linker with the sequence 5' Pso atg cga gaa agt gat aaa aaa aaa aaa CC Pu (where Pu is Puromycin-CPG [Glen Research]; C is a standard 3'-amidite [Glen Research]; a, t, c, and g are 5'-phosphoramidites [Glen Research]; and Pso is a psoralen C6 phosphoramidite [Gen Research]) was constructed according to standard manufacturer protocols. The linker was then photocrosslinked to an RNA with the target sequence 5' . . . GUA UAC GCU CUU UCA CUA (SEQ ID NO: 13) using the photocrosslinking techniques described above. This RNA-linker construct (with and without prior treatment with RNase H) was then successfully used for the synthesis of RNA-protein fusions.

One advantage of the photochemical methods for attaching a peptide acceptor to an RNA is that these methods do not require chemical modification of the RNA prior to ligation. This makes the process very robust and selective, and allows the use of an RNA from a crude T7 transcription reaction as the substrate for the chemical ligation.

EXAMPLE 6

Photocleavable Biotin-based RNA Purification and Ligation

If desired, an affinity-based RNA purification step may be combined with a photochemical ligation procedure described above (FIG. 7H). A suitable linker molecule is modified at its puromycin terminus with a photocleavable biotin moiety (e.g., EZ-Link™ NHS-PC-LC-Biotin, Pierce, Rockford, Ill.). The target RNA (obtained, for example, from a crude transcription reaction) is then hybridized to a defined amount of linker, and the resulting duplex is captured on a solid support, such as streptavidin (or a related) resin. The excess RNA, as well as the components of the transcription reaction are then removed by extensive washing. Irradiation with long-wave UV light simultaneously leads to photocrosslink formation and product release from the resin. The ligated RNA can then be directly fed into a translation and fusion formation reaction, without further purification.

This method is advantageous over previous RNA purification schemes. For example, after transcription, the amount of RNA merely has to be estimated to exceed the amount of linker used. When subjected to the described procedure, its amount is automatically reduced to a quantity not more than the amount of linker used. This, in turn, allows one to proceed to the next step without further quantization of the RNA (or ligated RNA) by, for example, taking $A_{260}$ UV readings, and the RNA amounts do not have to be adjusted otherwise. The nucleic-acid protein fusion molecule preparation process is therefore more suitable for automation.

In one exemplary technique, this biotin-based RNA purification and ligation protocol may be carried out as follows. In this photocleavable biotin-based RNA purification and ligation procedure, the linker is first biotinylated. The linker C6-psoralen-2-OMe[U AGC GGA UGC] $dA_{18}$ $TEG_2$ dCdC-puromycin (SEQ ID NO: 14) is biotinylated by combining 100 μl of 100 μM linker (10 nmol total), 50 μl of 1 umole EZ-Link™ PC-LC-Biotin in DMSO, 20 μl of 10×PBS, pH 7.4, and 30 μl $H_2O$. The mixture is incubated at room temperature for 2 hours, and results in a quantitative yield. The mixture is then precipitated twice with ethanol, with an expected recovery of >90% of the PC-biotinylated linker, and resuspended in 200 μl $H_2O$.

RNA is next transcribed using, for example, the T7 Megashortscript Kit (Ambion). Transcription is carried out using 10 pmole of a DNA template containing the sequence GCA UCC GCU AUU UAA $A_n$ (SEQ ID NO: 15) at the 3'-terminus for a 250 μl reaction. This transcription reaction should yield approximately 2–5 nmol of crude RNA product. No purification (phenol extraction, NAP-5 column, or RNeasy column) is required prior to proceeding to the next step.

In the next step of this purification and ligation technique, the biotinylated linker (10 μl of 50 pmol/μl biotinylated linker; 500 pmol total) is annealed to 62.5 to 250 μl of the transcription mixture (containing an estimated minimum of 500 pmole of RNA) using, for example, a PCR machine (heating for 30 seconds to 80° C., then cooling to 4° C. at 0.3° C./sec) with 15 μl of 5 M NaCl a final concentration of 0.25 M for a 300 μl reaction) and $H_2O$, to a final reaction volume of 300 μl. The RNA of the reaction mixture is next immobilized onto 100 μl of Neutravidin beads (Pierce, Rockford, Ill.) by gently rocking the reaction mixture at 4° C. for 30 minutes. The beads are then washed and resuspended in 300 μl $H_2O$.

The beads are next spun down and washed 3 times with 100 μl of buffer (25 mM Tris pH 7.0 and 0.25 M NaCl). Then the beads are UV irradiated for 15 minutes at room temperature (using a hand-held UV lamp UVGL-25; a microcentrifuge tube containing the beads is put directly on the lamp) to chemically ligate the linker to the RNA and photo-release the ligated molecule from the beads. It is expected that 250 pmol of ligated RNA is photo-released. Seventy-five μof $H_2O$ is added to the tubes, the tubes are vortexed for 30 seconds, and the beads are spun down. The 75 μl supernatant, containing the ligated RNA/linker, is used for translation and formation of nucleic acid-protein fusion molecules.

The nucleic acid-protein fusion molecules are formed by combining the 75 μl of supernatant from the previous step, and combining it with 225 μl of the buffer components and lysate of the Rabbit Reticulocyte Lysate Kit (Ambion), and incubating the mixture for 30 minutes at 30° C. KCl and $MgCl_2$ are next added to final concentrations of 500 mM and 50 mM, respectively, and the reaction continues to incubate for 60 minutes at room temperature to produce the nucleic acid-protein fusion molecules.

EXAMPLE 7

Peptide Acceptor Attachment to an RNA Through Strong Non-Covalent Bonds

Figure 8A:
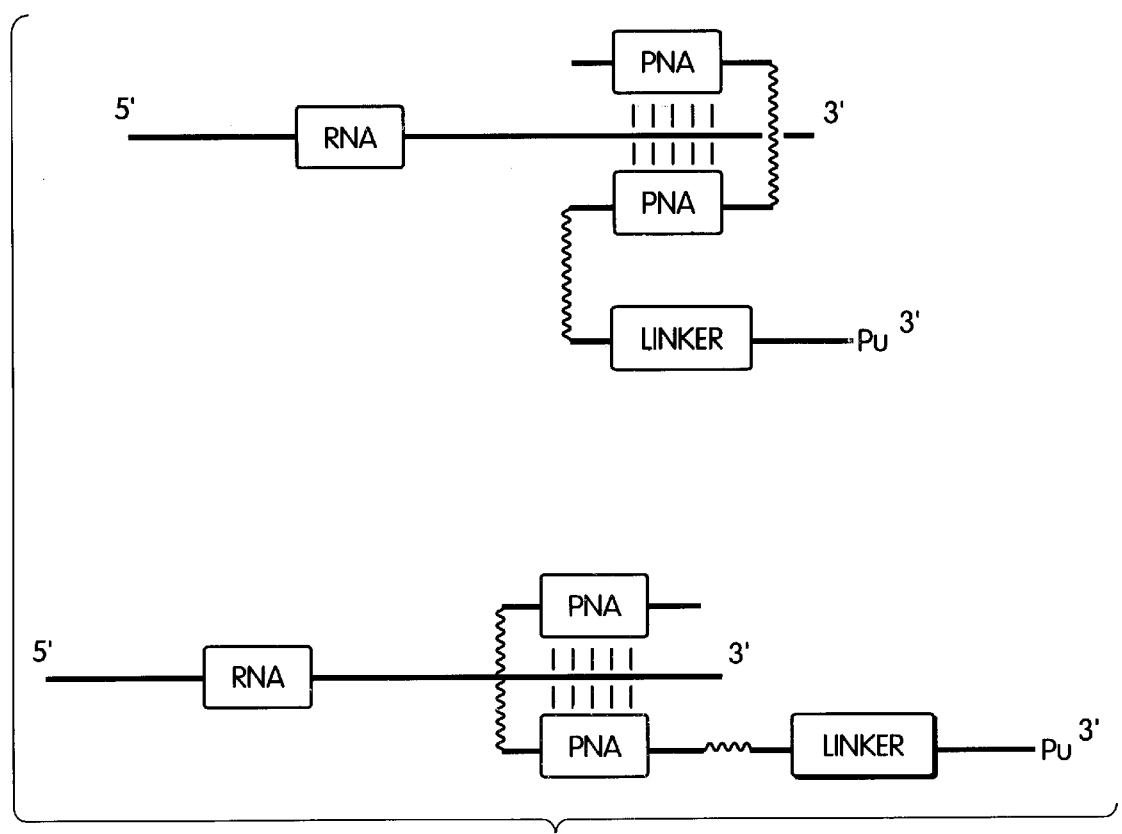
FIG. 8A is a schematic representation of the attachment of a puromycin linker to an RNA through $(PNA)_2$-RNA triplex formation. The puromycin linker is attached to two PNA molecules which bind to RNA forming a triple helix through strong non-covalent bonds.

As an alternative to covalent bond formation for the attachment of a peptide acceptor to an RNA molecule, methods relying solely on strong complex formation are also possible and are part of the present invention. One method involves the use of peptide nucleic acids (PNAs) for RNA recognition and binding, as shown in FIG. 8A. PNAs are DNA mimics comprising a backbone composed of achiral and uncharged N-(2-aminoethyl)glycine units (Knudsen and Nielsen, Nucleic Acids Res. 24:494,1996). PNAs have been shown to hybridize with sequence specificity and high affinity to complementary single-stranded DNA and to RNA. In particular, triple-helix-forming constructs comprising two PNA molecules binding to RNA, thereby forming a clamp, can provide an efficient means for strong binding of RNA, since such constructs can be extremely resistant to thermal denaturation and conditions used for in vitro translation (FIG. 8A) (Hanvey et al., Science, 258:1481, 1992).

The use of pseudoisocytosine bases further enhances stability at neutral and basic pH (Egholm et al, Nucleic Acids Res. 23:217, 1995). It has been demonstrated that such PNA-clamps remain associated with mRNA under in vitro translation conditions and cannot be displaced by the ribosome (Knudsen and Nielsen, Nucleic Acids Res. 24:494, 1996). This property maximizes the stability of the corresponding RNA-protein fusion constructs.

Figure 8B:
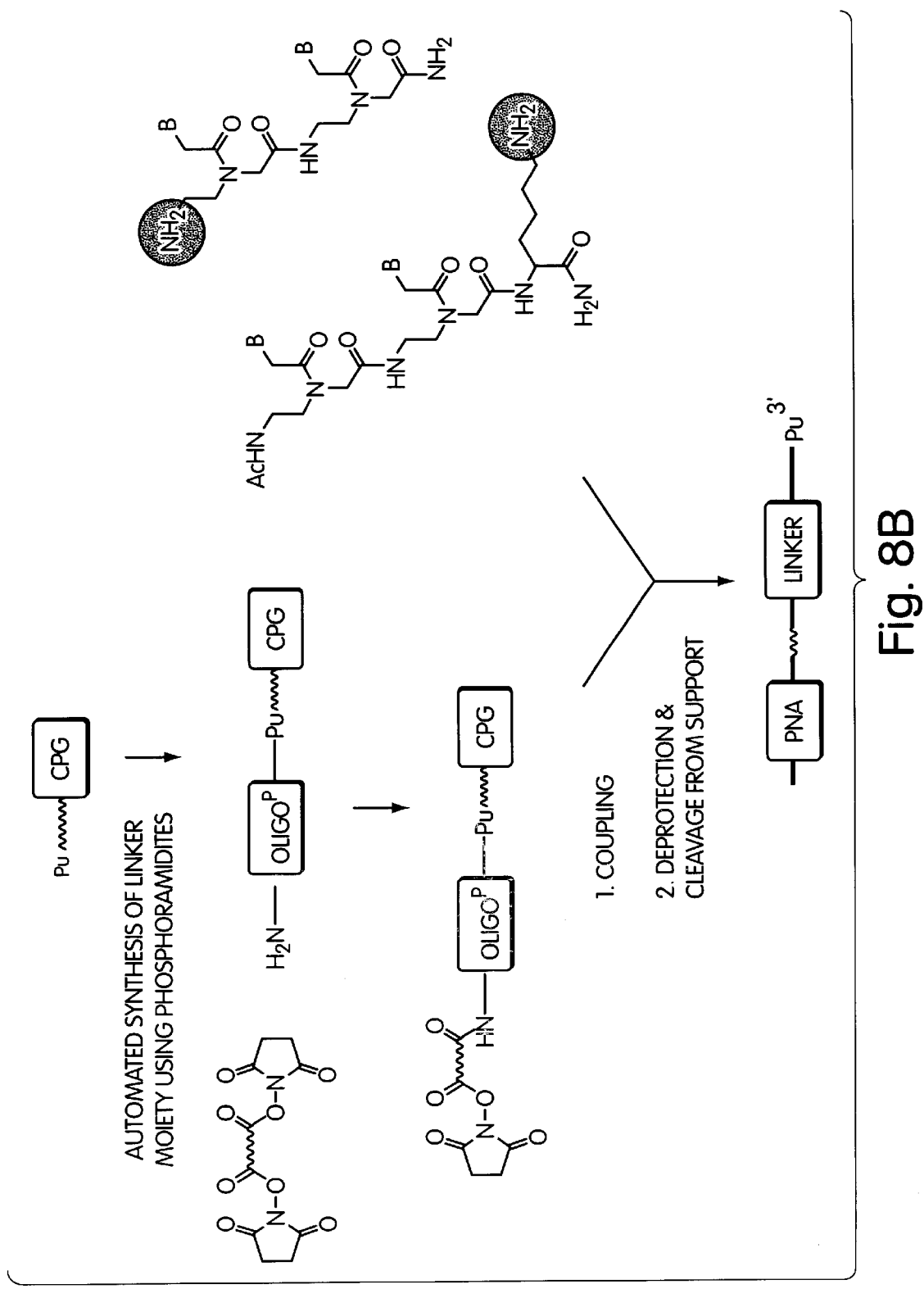
FIG. 8B is a schematic representation of steps involved in the synthesis of PNA-linker conjugates. The linker is attached to a solid support and modified to attach to the PNA. The PNA is then coupled to the desired linker, and the PNA linker molecule is deprotected and separated from the solid support.

The preparation of nucleic acid linker-PNA constructs may be accomplished by solid phase synthesis starting with puromycin-CPG, as shown in FIG. 8B and as described in Uhlmann et al. (Angew. Chem. Int. Ed. Engl. 35:2633, 1996). After assembly of the desired nucleic acid portion (or a PEG-spacer, if so desired) using standard automated synthesis, the solid phase synthesis is continued by attaching the PNA domain with the appropriate reagents (for example, as described in Uhlman et al. (supra)). Alternatively, the PNA can be pre-synthesized as a separate moiety (PE Biosystems, Foster City, Calif.), followed by chemical coupling to the desired linker portion.

In one particular example, a puromycin-DNA linker may be modified with a 5' terminal amino group, which can be further converted into a chemically activated ester (e.g., an NHS-ester through reaction with disuccinimidyl glutarate or related reagents; this technique is described, for example, in Cox et al. (J. Immunol. 145:1719, 1990); and pierce catalog Pierce, Rockford, Ill.). Subsequent reaction with the PNA moiety (having either an unprotected amino-terminus or a carboxy-terminal lysine) covalently links the domains. This process may be carried out in a homogenous solution containing the final DNA-linker product, or with the DNA bearing protecting groups and remaining attached to the solid resin.

EXAMPLE 8

Optimization of Linker Length and Composition

For all of the strategies described above, it is preferable to optimize the linker construct. Factors to be considered, for example, are the potential inclusion of template/target recognition elements and the steric accessibility of attached functional groups. Particularly when template or target recognition through nucleic acid hybridization is involved, factors including the target sequence and the chemical nature of the linker are preferably optimized. For example, RNA hybridization strength and consequently ligation efficiency are known to be increased by the use of 2-OMe RNA or propyne-modified nucleobases, rather than DNA (as described, for example, in Inoue et al., Nucleic Acids Res. 15:6131, 1987); Kibler-Herzog et al., Nucleic Acids Res. 19:2979, 1991; and Wagner et al., Science 260:1510, 1993).

The linkers may also be optimized for their effectiveness in the RNA-protein fusion reaction. This will generally involve varying the length of the linker, but may also involve the use of different building blocks for RNA-protein joining. In one particular example, the deoxynucleotides of the linker may be replaced with PEG-spacers or 2-OMe-RNA units (both from Glen Research, Sterling, Va.). Other embodiments are within the claims.

All patents and patent applications are hereby incorporated by reference.

What is claimed is:

1. A method of affixing a peptide acceptor to an RNA molecule, comprising:
   (a) providing an RNA molecule; and
   (b) chemically ligating said peptide acceptor to said RNA molecule to form a covalent bond under conditions that do not require in vitro translation.

2. The method of claim 1, wherein said peptide acceptor is joined to a psoralen moiety and said chemical ligation step comprises crosslinking said peptide acceptor, through said psoralen moiety, to said RNA molecule.

3. The method of claim 2, wherein said crosslinking is achieved by UV light irradiation.

4. The method of claim 2, wherein said psoralen moiety is attached to said peptide acceptor through a linker.

5. The method of claim 4, wherein said psoralen moiety is positioned at the 5' terminus of said linker.

6. The method of claim 4, wherein said psoralen moiety is positioned at the 3' terminus of said linker.

7. The method of claim 4, wherein said psoralen moiety is positioned within said linker.

8. The method of claim 4, wherein said linker comprises a C6 alkyl chain.

9. The method of claim 4, wherein said RNA molecule contains a stop codon positioned proximal to its 3' end.

10. The method of claim 4, wherein said linker is between 25 and 40 nucleotide units in length.

11. The method of claim 1, wherein, prior to said crosslinking, said RNA is hybridized to said linker which further comprises a photocleavable moiety, and said hybridized RNA is immobilized to a solid support through said photocleavable moiety.

12. The method of claim 11, wherein said photocleavable moiety is biotin.

13. A method of affixing a peptide acceptor to an RNA molecule, comprising:
   (a) providing an RNA molecule, wherein said RNA molecule is functionalized; and
   (b) providing a peptide acceptor, wherein a functional group is attached to said peptide acceptor; and
   (c) chemically ligating said peptide acceptor to said RNA molecule.

14. The method of claim 13, wherein said RNA molecule is functionalized by $IO_4^-$ oxidation.

15. The method of claim 13, wherein said chemical ligation is carried out in the absence of an external template.

16. The method of claim 13, wherein said peptide acceptor is covalently bonded to a linker molecule and, prior to said chemical ligation step, said RNA molecule and said peptide acceptor are aligned using an external template, said external template hybridizing to the 3' end of said RNA molecule and to the 5' end of said linker molecule.

17. The method of claim 13, wherein said peptide acceptor is covalently bonded to a linker molecule and, prior to said chemical ligation step, said RNA molecule and said peptide acceptor are aligned by hybridization of said linker molecule to the 3' end of said RNA.

18. The method of claim 17, wherein said functional group of said peptide acceptor is located at the 5' end of said linker molecule.

19. The method of claim 17, wherein said functional group of said peptide acceptor is flanked by a region which hybridizes to said RNA molecule on one side and by said peptide acceptor on the other side.

20. The method of claim 13, wherein said peptide acceptor functional group is chosen from the group consisting of an amine, hydrazine, (thio)hydrazide, and (thio)semicarbazone.

21. A method of affixing a peptide acceptor to an RNA molecule, comprising:
   (a) attaching a functional group to an RNA molecule through reductive amination;
   (b) modifying a peptide acceptor to react with said functional group of said RNA molecule; and
   (c) contacting said peptide acceptor with said RNA molecule under conditions which allow covalent bond formation.

22. The method of claim 1, wherein said functional group is a thiol, maleirnide, or amine.

23. The method of claim 1, 13 or 21, wherein said RNA molecule comprises a translation initiation sequence and a start codon operably linked to a protein coding sequence.

24. The method of claim 1, 13 or 21, wherein said peptide acceptor is puromycin.

25. The method of claim 1, 13 or 21, wherein said peptide acceptor is covalently bonded to a non-nucleotide linker molecule.

26. The method of claim 25, wherein said linker comprises triethylene glycol spacers.

27. The method of claim 25, wherein said linker comprises 2'-OMe-RNA phosphoramidites.

28. The method of claim 1, 13 or 21, wherein said RNA or said linker contains an affinity purification sequence and said method further comprises purifying said RNA.

29. The method of claim 28, wherein said affinity purification sequence comprises a poly (A) sequence.

30. The method of claim 1, wherein said peptide acceptor is covalently bonded to a linker molecule.

31. An RNA molecule chemically ligated to a peptide acceptor, wherein said RNA molecule is crosslinked to said peptide acceptor and said RNA molecule contains a psoralen photocrosslink target site.

32. The RNA moelcule of claim 31, wherein said RNA contains a stop codon positioned at its photocrosslink target site.

33. The molecule of claim 31, wherein said peptide acceptor is ligated at the 3' end of said RNA molecule.

34. The molecule of claim 31, wherein said RNA molecule comprises a translation initiation sequence and a start codon operably linked to a protein coding sequence.

35. The molecule of claim 31, wherein said peptide acceptor is puromycin.

36. The RNA molecule of claim 31, wherein said RNA is crosslinked to said peptide acceptor through a psoralen moiety.

37. A method of generating an RNA-protein fusion, said method comprising:
   (a) providing an RNA molecule hybridized to a linker, said linker comprising a photocleavable moiety, a psoralen moiety, and a peptide acceptor;
   (b) immobilizing said RNA to a solid support under conditions in which non-immobilized RNA are substantially removed from the support;
   (c) crosslinking said peptide acceptor to said RNA, through said psoralen moiety, whereby said crosslinking simultaneously releases said crosslinked RNA from said solid support; and
   (d) translating the crosslinked RNA formed in step (c) to form an RNA fusion protein.

38. An RNA molecule covalently ligated to a peptide acceptor through a linker molecule of between 25–40 nucleotides.

39. An RNA molecule covalently ligated to a peptide acceptor through a linker molecule comprising non-nucleotide moieties.

40. The RNA molecule of claim 39, wherein said non-nucleotide moieties comprise polyethylene glycol.

41. The RNA molecule of claim 39, wherein said non-nucleotide moieties comprise 2'-OMe-RNA phosphoramidites.

42. An RNA molecule crosslinked to a peptide acceptor through a psoralen moiety.

43. The RNA molecule of claim 42, wherein said psoralen moiety is attached to said peptide acceptor through a linker.

* * * * *

SEQUENCE LISTING

<160> NUMBER OF SEQ ID NOS: 26

<210> SEQ ID NO 1
<211> LENGTH: 91
<212> TYPE: RNA
<213> ORGANISM: Artificial Sequence
<220> FEATURE:
<223> OTHER INFORMATION: designed sequence to act as an identifying tag

<400> SEQUENCE: 1
gggacaauua cuauuuacaa uuacaaugga cuacaaggac gaugacgaua agggcggcug       60
gucccacccc caguucgaga aggcauccgc u                                     91

<210> SEQ ID NO 2
<211> LENGTH: 38
<212> TYPE: DNA
<213> ORGANISM: Artificial Sequence
<220> FEATURE:
<223> OTHER INFORMATION: designed sequence to act as a linker

<400> SEQUENCE: 2
cgcggatgca aaaaaaaaa aaaaaaaaa aaaaaacc                                38

```
<210> SEQ ID NO 3
<211> LENGTH: 92
<212> TYPE: RNA
<213> ORGANISM: Artificial Sequence
<220> FEATURE:
<223> OTHER INFORMATION: designed sequence to act as an identifying tag

<400> SEQUENCE: 3
gggacaauua cuauuuacaa uuacaaugga cuacaaggac gaugacgaua agggcggcug        60
gucccacccc caguucgaga agaacggcua ua                                     92

<210> SEQ ID NO 4
<211> LENGTH: 39
<212> TYPE: DNA
<213> ORGANISM: Artificial Sequence
<220> FEATURE:
<223> OTHER INFORMATION: designed sequence to act as a linker

<400> SEQUENCE: 4
tagccgttct aaaaaaaaaa aaaaaaaaaa aaaaaaacc                              39

<210> SEQ ID NO 5
<211> LENGTH: 44
<212> TYPE: DNA
<213> ORGANISM: Artificial Sequence
<220> FEATURE:
<223> OTHER INFORMATION: designed sequence to act as a linker

<400> SEQUENCE: 5
tagccgttct tctcgaaaaa aaaaaaaaaa aaaaaaaaaa aacc                        44

<210> SEQ ID NO 6
<211> LENGTH: 35
<212> TYPE: RNA
<213> ORGANISM: Artificial Sequence
<220> FEATURE:
<223> OTHER INFORMATION: designed sequence to act as a target for a
      linker

<400> SEQUENCE: 6
gacuacaagg acgaggcauc cgcucuuuca cuaua                                  35

<210> SEQ ID NO 7
<211> LENGTH: 12
<212> TYPE: RNA
<213> ORGANISM: Artificial Sequence
<220> FEATURE:
<223> OTHER INFORMATION: designed sequence to act as a target for a
      linker

<400> SEQUENCE: 7
gcauccgcua uu                                                           12

<210> SEQ ID NO 8
<211> LENGTH: 8
<212> TYPE: PRT
<213> ORGANISM: Artificial Sequence
<220> FEATURE:
<223> OTHER INFORMATION: designed sequence to act as an identifying tag

<400> SEQUENCE: 8

Asp Tyr Lys Asp Asp Asp Asp Lys
  1               5

<210> SEQ ID NO 9
```

```
<211> LENGTH: 8
<212> TYPE: PRT
<213> ORGANISM: Artificial Sequence
<220> FEATURE:
<223> OTHER INFORMATION: designed sequence to act as an identifying tag

<400> SEQUENCE: 9

Trp Ser His Pro Gln Phe Glu Lys
 1               5

<210> SEQ ID NO 10
<211> LENGTH: 47
<212> TYPE: DNA
<213> ORGANISM: Artificial Sequence
<220> FEATURE:
<223> OTHER INFORMATION: sequence designed to act as a linker

<400> SEQUENCE: 10
cgtaggcgag aaagtgataa aaaaaaaaaa aaaaaaaaa aaaaacc                    47

<210> SEQ ID NO 11
<211> LENGTH: 20
<212> TYPE: RNA
<213> ORGANISM: Artificial Sequence
<220> FEATURE:
<223> OTHER INFORMATION: designed sequence to act as a target for a
      linker

<400> SEQUENCE: 11
gcauccgcuc uuucacuaua                                                 20

<210> SEQ ID NO 12
<211> LENGTH: 29
<212> TYPE: DNA
<213> ORGANISM: Artificial Sequence
<220> FEATURE:
<223> OTHER INFORMATION: designed sequence to act as a linker

<400> SEQUENCE: 12
atgcgagaaa gtgataaaaa aaaaaaacc                                       29

<210> SEQ ID NO 13
<211> LENGTH: 18
<212> TYPE: RNA
<213> ORGANISM: Artificial Sequence
<220> FEATURE:
<223> OTHER INFORMATION: designed sequence to act as a target for a
      linker

<400> SEQUENCE: 13
guauacgcuc uuucacua                                                   18

<210> SEQ ID NO 14
<211> LENGTH: 32
<212> TYPE: RNA
<213> ORGANISM: Artificial Sequence
<220> FEATURE:
<223> OTHER INFORMATION: designed sequence to act as a linker

<400> SEQUENCE: 14
uagcggaugc aaaaaaaaaa aaaaaaaaaa aa                                   32

<210> SEQ ID NO 15
<211> LENGTH: 16
<212> TYPE: RNA
<213> ORGANISM: Artificial Sequence
<220> FEATURE:
```

```
<223> OTHER INFORMATION: designed sequence as a template for in vitro
      transcription

<400> SEQUENCE: 15
gcauccgcua uuuaaa                                                        16

<210> SEQ ID NO 16
<211> LENGTH: 10
<212> TYPE: DNA
<213> ORGANISM: Artificial Sequence
<220> FEATURE:
<223> OTHER INFORMATION: designed sequence for nucleic acid purification

<400> SEQUENCE: 16
aaaaaaaaaa                                                               10

<210> SEQ ID NO 17
<211> LENGTH: 11
<212> TYPE: DNA
<213> ORGANISM: Artificial Sequence
<220> FEATURE:
<223> OTHER INFORMATION: designed sequence for nucleic acid purification

<400> SEQUENCE: 17
aaaaaaaaaa a                                                             11

<210> SEQ ID NO 18
<211> LENGTH: 12
<212> TYPE: DNA
<213> ORGANISM: Artificial Sequence
<220> FEATURE:
<223> OTHER INFORMATION: designed sequence for nucleic acid purification

<400> SEQUENCE: 18
aaaaaaaaaa aa                                                            12

<210> SEQ ID NO 19
<211> LENGTH: 13
<212> TYPE: DNA
<213> ORGANISM: Artificial Sequence
<220> FEATURE:
<223> OTHER INFORMATION: designed sequence for nucleic acid purification

<400> SEQUENCE: 19
aaaaaaaaaa aaa                                                           13

<210> SEQ ID NO 20
<211> LENGTH: 14
<212> TYPE: DNA
<213> ORGANISM: Artificial Sequence
<220> FEATURE:
<223> OTHER INFORMATION: designed sequence for nucleic acid purification

<400> SEQUENCE: 20
aaaaaaaaaa aaaa                                                          14

<210> SEQ ID NO 21
<211> LENGTH: 15
<212> TYPE: DNA
<213> ORGANISM: Artificial Sequence
<220> FEATURE:
<223> OTHER INFORMATION: designed sequence for nucleic acid purification

<400> SEQUENCE: 21
aaaaaaaaaa aaaaa                                                         15
```

-continued

```
<210> SEQ ID NO 22
<211> LENGTH: 16
<212> TYPE: DNA
<213> ORGANISM: Artificial Sequence
<220> FEATURE:
<223> OTHER INFORMATION: designed sequence for nucleic acid purification

<400> SEQUENCE: 22
aaaaaaaaaa aaaaaa                                                    16

<210> SEQ ID NO 23
<211> LENGTH: 17
<212> TYPE: DNA
<213> ORGANISM: Artificial Sequence
<220> FEATURE:
<223> OTHER INFORMATION: designed sequence for nucleic acid purification

<400> SEQUENCE: 23
aaaaaaaaaa aaaaaaa                                                   17

<210> SEQ ID NO 24
<211> LENGTH: 18
<212> TYPE: DNA
<213> ORGANISM: Artificial Sequence
<220> FEATURE:
<223> OTHER INFORMATION: designed sequence for nucleic acid purification

<400> SEQUENCE: 24
aaaaaaaaaa aaaaaaaa                                                  18

<210> SEQ ID NO 25
<211> LENGTH: 19
<212> TYPE: DNA
<213> ORGANISM: Artificial Sequence
<220> FEATURE:
<223> OTHER INFORMATION: designed sequence for nucleic acid purification

<400> SEQUENCE: 25
aaaaaaaaaa aaaaaaaaa                                                 19

<210> SEQ ID NO 26
<211> LENGTH: 20
<212> TYPE: DNA
<213> ORGANISM: Artificial Sequence
<220> FEATURE:
<223> OTHER INFORMATION: designed sequence for nucleic acid purification

<400> SEQUENCE: 26
aaaaaaaaaa aaaaaaaaaa                                                20
```